United States Patent [19]
Kawakami et al.

[11] Patent Number: 5,769,085
[45] Date of Patent: Jun. 23, 1998

[54] APPARATUS FOR DETECTING AWARENESS OF A VEHICLE DRIVER AND METHOD THEREOF

[75] Inventors: Yoshinaka Kawakami, Kariya; Yoshiharu Takigawa, Okazaki; Kouichi Kamiya, Anjo; Katsunori Hamatani, Okazaki; Eiji Sato, Nishikamo-gun; Yasufumi Sekine, Okazaki, all of Japan

[73] Assignee: Mitsubishi Jidosha Kogyo Kabushiki Kaisha, Tokyo, Japan

[21] Appl. No.: 633,558

[22] Filed: Apr. 17, 1996

Related U.S. Application Data

[63] Continuation of Ser. No. 177,862, Jan. 4, 1994, abandoned.

[30] Foreign Application Priority Data

Jan. 6, 1993 [JP] Japan ..................... 5-000784
Jan. 6, 1993 [JP] Japan ..................... 5-000787

[51] Int. Cl.$^6$ .................................................. A61B 5/024
[52] U.S. Cl. ............................................................ 128/706
[58] Field of Search ................................. 128/706, 707, 128/708, 709, 700

[56] References Cited

U.S. PATENT DOCUMENTS 4,425,921 1/1984 Fujisaki et al. ..................... 128/700
4,572,207 2/1986 Yoshimi et al. .
4,860,759 8/1989 Kahn et al. ........................ 128/700

FOREIGN PATENT DOCUMENTS

| 2485364 | 6/1980 | France . |
| 2555042 | 6/1977 | Germany . |
| 612340 | 7/1979 | Germany . |
| 3826943 | 2/1990 | Germany . |
| 59-22537 | 7/1982 | Japan . |
| 59-25729 | 7/1982 | Japan . |
| 59-214429 | 5/1983 | Japan . |
| 62-9404 | 7/1985 | Japan . |
| 26231 | 6/1988 | Japan . |
| 2159111 | 11/1985 | United Kingdom . |

*Primary Examiner*—Scott M. Getzow

[57] ABSTRACT

A heartbeat rate detection apparatus and method which can accurately detect a heartbeat of a driver by simultaneously detecting a heartbeat rate of the driver with an infrared sensor, and detecting a heartbeat rate of the driver from a potential difference due to pulsation between both hands with a potencial type heartbeat sensor, comparing the the heartbeat rate detected by the infrared type heartbeat sensor with the heartbeat rate detected by the potential type heartbeat sensor, and selects one as an effective heartbeat rate.

26 Claims, 34 Drawing Sheets

5,769,085

APPARATUS FOR DETECTING AWARENESS OF A VEHICLE DRIVER AND METHOD THEREOF

This application is a continuation of application Ser. No. 08/177,862 filed on Jan. 4, 1994, now abandoned.

BACKGROUND OF THE INVENTION

This invention relates to an apparatus and method for improving the awareness of vehicle drivers based on heartbeat rate detection. This invention is applicable to persons such as a vehicle driver or a pilot of a ship or airplane.

Recently, as a result of road network improvements, the moving ability of vehicles has been considerably improved and more people spend a considerable amount of time driving. In general, drivers tend to drive their vehicle regardless of whether they are tired. If the driver operates the vehicle for an extended time without rest, fatigue sets in, which leads to decreased awareness of the driver, and therefore, the possibility of an accident occurring, increases.

To prevent this, an apparatus for improving the awareness of vehicle drivers has been proposed which requires a response from the driver is provided at a time interval, and a decrease in driver awareness is determined from the driver's response time to the given warning. However, with such a prior art apparatus, a response may be required during traveling on a city road or curved road where the driver must concentrate on driving, and therefore the driver's response time may be long even though the driver's awareness level is high.

Other conventional apparatus monitor the driver's physical condition and, when a normal operation limit is exceeded, the driver is notified. In general, a heartbeat rate is increased or decreased according to driving force, mental stress, or a sensation of fear. Therefore, to determine the level of awareness of the driver, the driver's heartbeat rate during operation of the vehicle is detected by a heartbeat sensor, and the period of the heartbeat rate is sequentially calculated and converted to determine whether or not the value is within an acceptable range.

For example, Japanese Patent Publication Laid-open (Japanese OPI) 59-22537 discloses an apparatus for detecting the heartbeat rate of the driver during operation of the vehicle using a heartbeat sensor. In this apparatus, a steering wheel has an infrared type heartbeat sensor, which includes a light emitting diode for emitting light and a phototransistor for receiving light, wherein the light emitted by the light emitting diode is reflected by blood flowing through vessels in the driver's thumb and applied to the phototransistor, and a light receiving signal is generated whose level corresponds to the amount of incident light, in order to detect changes in blood flow of the driver.

Further, a heartbeat sensor of another type is disclosed in Japanese OPI 59-25729 or 59-214429. The steering wheel has a potential type heartbeat sensor mounted therein, which includes at least two electrodes for detecting the driver's heartbeat rate from a period of an electrocardiographic waveform between both hands of the driver or a number of pulses in a reference time.

Further, Japanese OPI 62-9404 discloses calculating a simple average of a heartbeat output, and comparing the simple average with a predetermined reference heartbeat rate to detect a decrease in activity level of the driver.

Japanese OPI 2-6231 discloses an apparatus in which an average value and a variance of a driver's heartbeat rate are calculated from a heartbeat sensor, and driver fatigue is determined by integrating the calculated result in order to determine an abnormality.

However, the above-described prior art infrared type heartbeat rate detection apparatus has a problem in that when the phototransistor of the heartbeat sensor mounted on the steering wheel receives intense sunlight, the heartbeat sensor misoperates and makes it impossible to exactly detect the heartbeat rate of the driver. The heartbeat sensor is mounted at any position of the steering wheel and, if not contacted closely with the finger, external light between the finger and the heartbeat sensor (phototransistor) deteriorates the detection accuracy of the heartbeat rate. Further, when the finger pressure on the heartbeat sensor is too high, the vessel under the skin is pressed thereby disturbing the blood flow, and making it impossible to exactly detect the heartbeat rate.

Further, in the above potential type heartbeat rate detection apparatus, the driver cannot detect the heartbeat rate unless the steering wheel is gripped by both hands. If the driver operates the vehicle for an extended time without rest, fatigue sets in, leading to a decrease in concentration, the driver reduces the force of gripping the steering wheel, or does not grip the steering wheel with both hands, and the heartbeat rate cannot be detected.

Further, when the output of the heartbeat sensor is simply averaged, it is possible to reduce measurement errors by the heartbeat sensor, but basically impossible to eliminate errors due to fluctuations in the heartbeat rate associated with respiration of the driver, making it difficult to obtain reliable heartbeat rate data. Therefore, a determination of decreased driver awareness may be erroneous.

A primary object of the present invention is to provide a high-precision heartbeat rate detection apparatus, which can positively detect the heartbeat rate of the driver which eliminates the above-identified problems.

SUMMARY OF THE INVENTION

In accordance with the present invention which attains the above object, there is provided a heartbeat rate detection apparatus comprising: an infrared type heartbeat sensor for detecting a heartbeat rate of a driver, a potential type heartbeat sensor for detecting the heartbeat rate of the driver from a potential difference due to pulsation between both hands, and heartbeat data processing means for comparing the heartbeat rate detected by the infrared type heartbeat sensor with the heartbeat rate detected by the potential type heartbeat sensor, and selecting one as an effective heartbeat rate.

Therefore, when the driver grips the steering wheel, the infrared type heartbeat sensor detects the heartbeat rate of the driver from infrared light projected by the light projector to the driver's hand, which is reflected by pulsating blood and received by a light receiver and, at the same time, the potential type heartbeat sensor detects the heartbeat rate of the driver from a potential difference due to polsating blood detected by contacting the individual electrodes with both hands of the driver, and the heartbeat data processing means compares heartbeat rate detected by the infrared type heartbeat sensor with heartbeat rate detected by the potential type heartbeat sensor, and selects one as an effective heartbeat rate.

Further, the heartbeat rate detection apparatus of the present invention comprises: a heartbeat sensor for detecting a heartbeat rate, and heartbeat data processing means for determining an average heartbeat rate by eliminating driver respiration variations from the detected heartbeat rate.

Therefore, errors from changes in the heartbeat rate due to driver respiration variations can be eliminated.

In the heartbeat rate detection apparatus of the present invention, the detected heartbeat rate is determined from heartbeat pulse intervals and the heartbeat data processing means determines the average heartbeat rate from at least two heartbeat.

There is further provided according to the present invention a method comprising the steps of: determining a heartbeat rate from an infrared type heartbeat sensor; determining a heartbeat rate from a potential type heartbeat sensor; and selecting one as an effective heartbeat rate.

DETAILED DESCRIPTION OF THE PREFERRED EMBODIMENTS

An embodiment of the present invention will now be described in detail with reference to the drawings.

Figure 1:
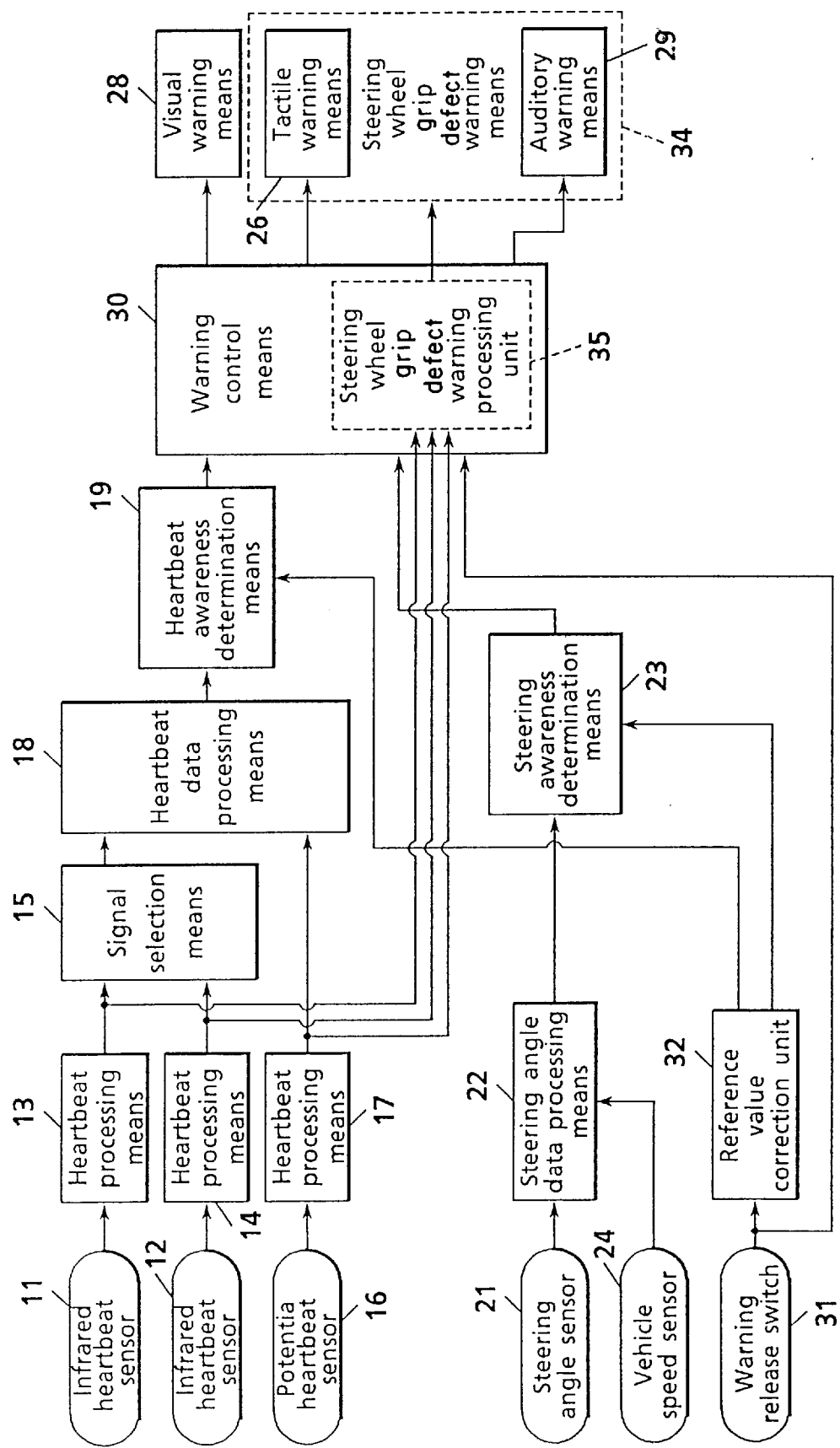
FIG. 1 is a block diagram showing the structure of an embodiment of the apparatus for improving the awareness of vehicle drivers according to the present invention.
Figure 2:
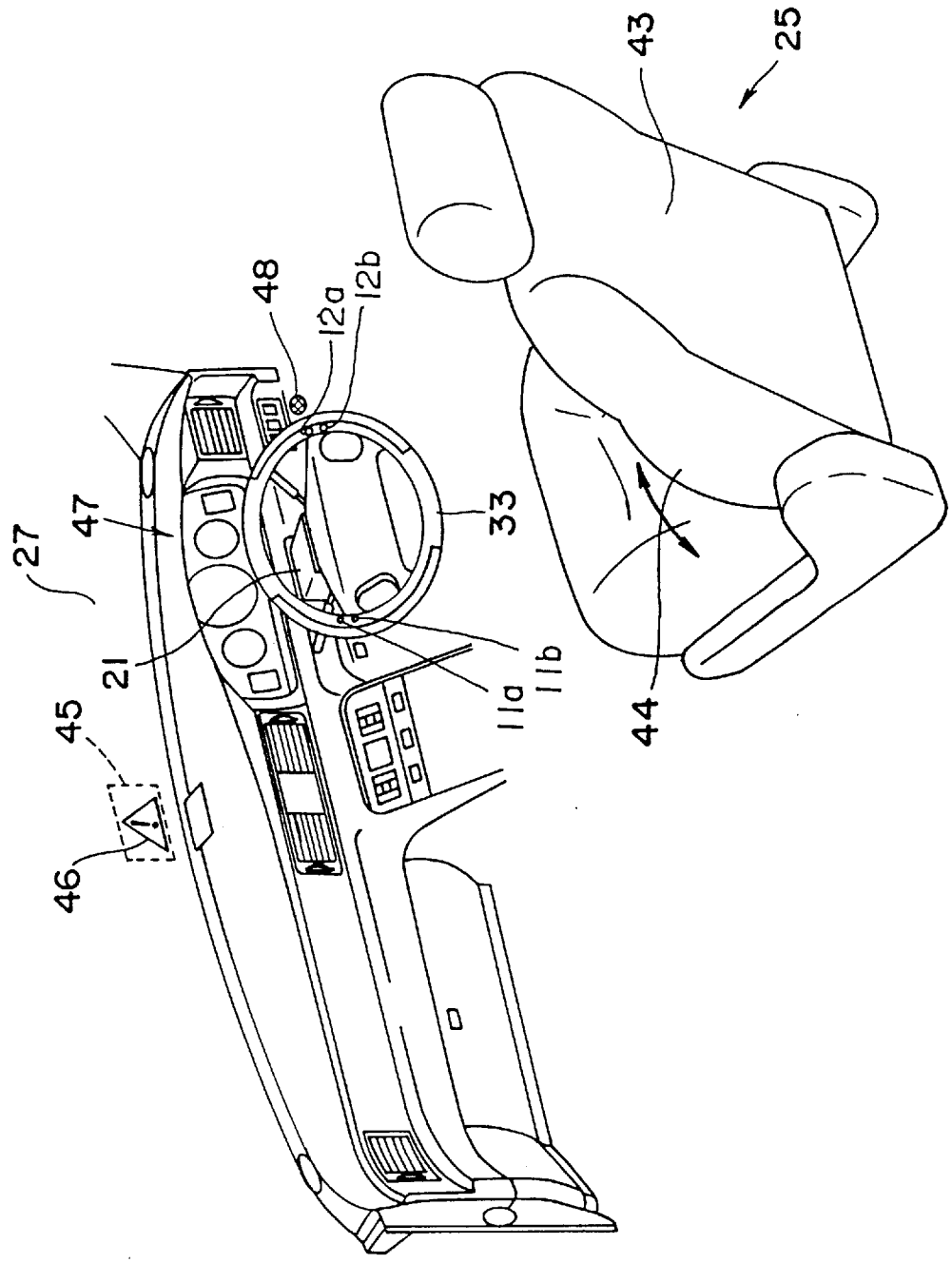
FIG. 2 is a schematic perspective view showing appearance of a vehicle interior in the embodiment.

FIG. 1 is a flow chart of an embodiment in which the awareness determination apparatus of the present invention is applied to an apparatus for improving the awareness of vehicle drivers, and FIG. 2 is a schematic view showing the interior of the vehicle room in this embodiment. A pair of right and left infrared heartbeat sensors 11 and 12 for detecting heartbeat pulses of the driver (not shown) are connected with heartbeat processing means 13 and 14 for receiving detection signals from the infrared heartbeat sensors 11 and 12 and calculating a heartbeat rate of the driver, and the heartbeat processing means 13 and 14 are connected to signal selection means 15, which selects either one of the signals from the heartbeat processing means 13 or 14. A potential heartbeat sensor 16, which is different from the heartbeat sensors 11 and 12, is connected to heartbeat processing means 17 which receives a detection signal from the potential heartbeat sensor 16 and calculates a heartbeat rate of the driver. The signal selection means 15 and the heartbeat processing means 17 are connected with heartbeat data processing means 18 for calculating an average value of the driver's heartbeat rate and a variance thereof according to output signals from the signal selection means 15 and the heartbeat processing means 17, and the heartbeat data processing means 18 is connected to heartbeat awareness determination means 19 for determining an awareness of the driver according to the calculations made by the heartbeat data processing means 18.

Further, a steering angle sensor 21 for detecting a deviation from a neutral position of a steering shaft 20 (hereinafter referred to as "steering angle") is connected to steering angle data processing means 22 which receives a detection signal from the steering angle sensor 21 and calculates a parameter of frequency analyzed steering component, and the steering angle data processing means 22 is connected to steering awareness determination means 23 for determining an awareness of the driver according to a calculated result from the steering angle data processing means 22.

Further, the steering angle data processing means 22 of the present embodiment is connected to a vehicle speed sensor 24 for detecting a traveling speed (hereinafter referred to as "vehicle speed") of the vehicle, and a detection signal from the vehicle speed sensor 24 is also input to the steering angle data processing means 22.

Further, the vehicle of the present embodiment is provided with tactile warning means 26 for generating a warning according to deformation of a driver's seat 25, and visual warning means 28 for displaying a warning on a front window 27 of the vehicle, and auditory warning means 29 for generating an audible. These three warning means 26, 28, and 29 are connected to the heartbeat awareness determination means 19 and the steering awareness determination means 23, wherein awareness signals are generated by the heartbeat awareness determination means 19 and the steering awareness determination means 23, and data reflecting the awareness of the driver, are output to warning control means 30, and the warning control means 30 controls operation of the three warning means 26, 28, and 29 according to the awareness signals generated by the heartbeat awareness determination means 19 and the steering awareness determination means 23.

In addition, a warning release switch 31 is provided in the vehicle interior for the driver to terminate warnings output by the three warning means 26, 28, and 29, and the warning release switch 31 is connected to the warning control means 30 and a reference value correction unit 32. The reference value correction unit 32 is connected to the heartbeat awareness determination means 19 and the steering awareness determination means 23, and data calculated by the reference value correction unit 32 is input to the heartbeat awareness determination means 19 and the steering awareness determination means 23.

In the present embodiment, the above two types of heartbeat sensors 11, 12, and 16 are individually mounted at predetermined positions on a steering wheel 33. Therefore, a mechanism for prompting the driver to grip the steering wheel 33 correctly is provided, because the driver's heartbeat pulse cannot be detected, especially with the potential heartbeat sensor 16, unless the driver grips the steering wheel 33 with both hands at the predetermined positions.

Specifically, the vehicle of the present embodiment is provided with steering wheel grip defect warning means 34 whose operation is controlled by the warning control means 30. The steering wheel grip defect warning means 34 of the present embodiment uses the two warning means 26 and 29. Further, warning control means 30 includes a steering wheel grip defect warning processing unit 35 which receives output signals from the heartbeat processing means 13, 14, and 17 to determine whether or not the driver is griping the steering wheel 33 correctly according to output signals from the heartbeat processing means 13, 14, and 17. The warning control means 30 operates the steering wheel grip defect warning means 34 when it is determined that the driver is not gripping the steering wheel 33 correctly, and automatically stops operation of the steering wheel grip defect warning means 34 when it is determined that the driver is gripping the steering wheel 33 correctly.

Figure 3:
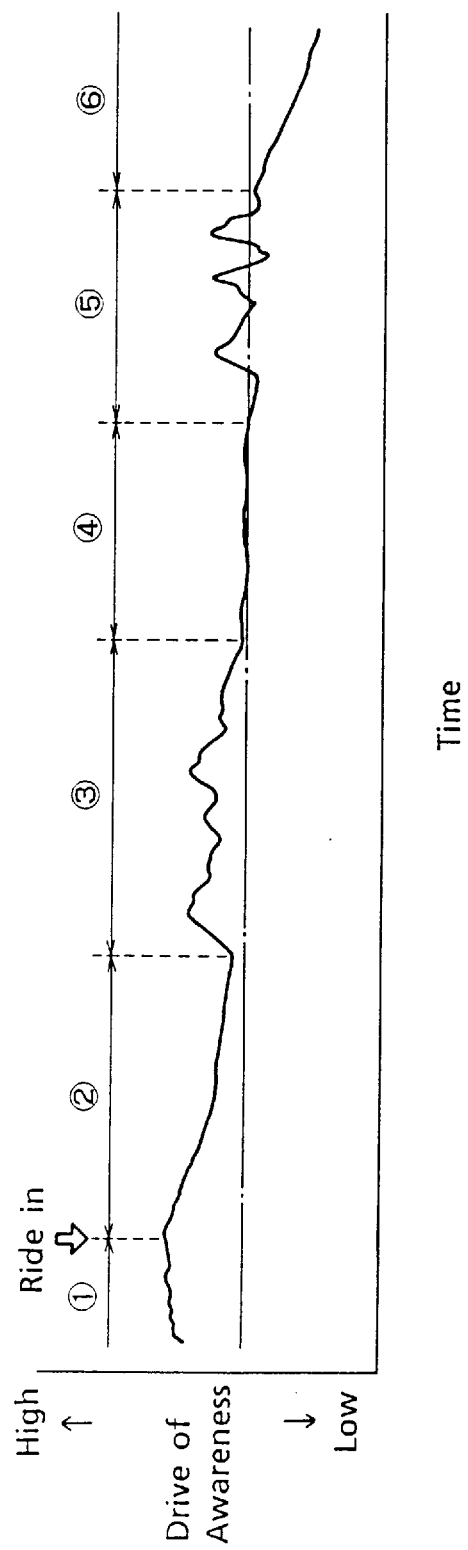
FIG. 3 is a graph showing changes in driver awareness over time.

In general, it is well known that driver awareness gradually decreases during a trip and the decrease is often accelerated due to traveling on a monotonous, deseated road for an extended time. An example of changes over time in driver awareness is illustrated in FIG. 3. The area (1) indicates a period before the trip, (2) indicates an awareness decreasing area as a result of continued driving, (3) indicates an area where awareness increases due to stress resulting from beginning the trip or stress from driving on a city road, (4) indicates an area where awareness is stable during traveling on a less crowded, monotonous road or a highway, (5) indicates an area where the awareness of the driver varies because the driver feels sleepy, and (6) indicates an area where the driver is completely unaware because the driver is asleep.

As can be seen from FIG. 3, normally there is an area (5) where the driver awareness increases and decreases because the driver feels sleepy before an area (6) where the driver actually falls asleep, and there is an area (4) where the awareness of the driver is stable before the driver begins to feel sleepy. That is, the awareness of the driver may be continuously monitored to estimate the area of stable awareness, and a transition area where the driver's awareness varies a great deal may be predicted from the area of stable awareness, and a warning can be output to prevent the driver from falling asleep.

Figure 4:
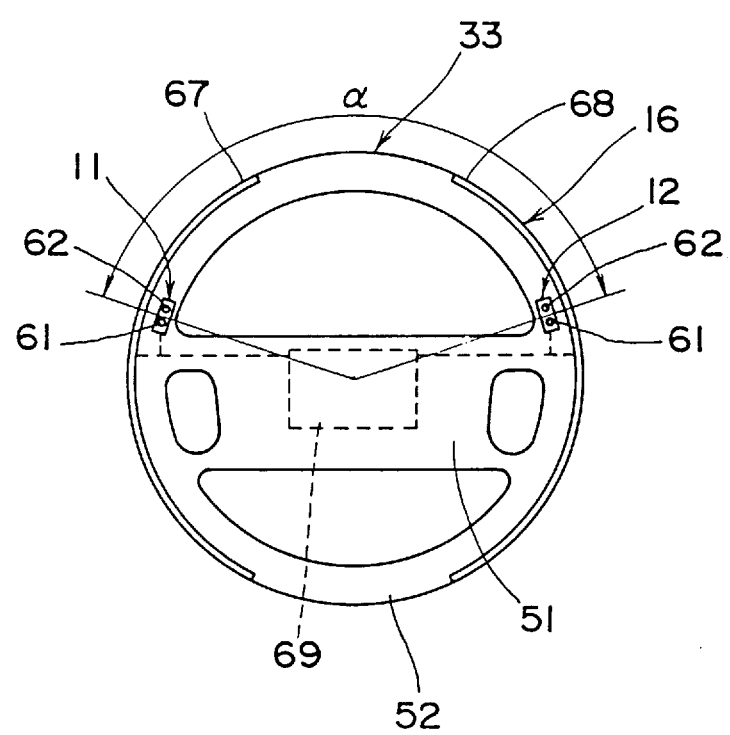
FIG. 4 is a schematic front view of a steering wheel.

Based on these findings, the changes in awareness shown in FIG. 3 can be estimated according to detection signals from the two types of heartbeat sensors 11, 12, and 16, in the illustrated positions of the steering wheel 33 in FIG. 4.

The infrared type heartbeat sensors 11 and 12 which function independently, detect the pulsation of blood in vessel is using infrared light. The potential type heartbeat sensor 16 detects a pulsed blood potential difference between both hands of the driver. The infrared type heartbeat sensors 11 and 12 may malfunction in strong sunlight and, the potential type heartbeat sensor 16 cannot detect the heartbeat rate if the driver does not grip the steering wheel with both hands. As a result, the two types of heartbeat sensors 11, 12, and 16 are combined to accurately detect the heartbeat rate of the driver.

Figure 5:
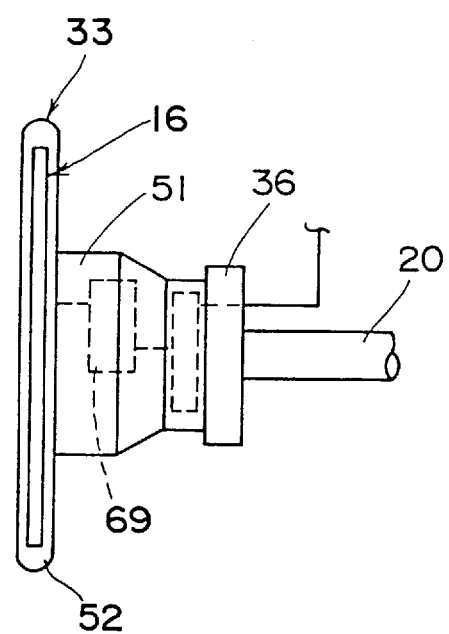
FIG. 5 is a schematic side view of the steering wheel.

As shown in FIGS. 4 and 5, the steering wheel 33 is rotatably mounted to a steering column 36, and includes a steering shaft 20, a hub 51, and a round wheel 52. The infrared type heartbeat sensors 11 and 12 and the potential type heartbeat sensor 16 are mounted on the wheel 52 of the steering wheel 33.

The infrared type heartbeat sensors 11 and 12, include an infrared light emitting diode 61 as a light emitter and a phototransistor 62 as a light receiver and are mounted individually at positions where the driver grips the steering wheel 33 naturally with right and left hands, that is, two positions indicating a time of 10:10 on a clock of the steering wheel 33, two straight lines extending from the center of the steering wheel 33 to the individual heartbeat sensors 11 and 12 making an angle a of about 120 degrees.

Figure 6:
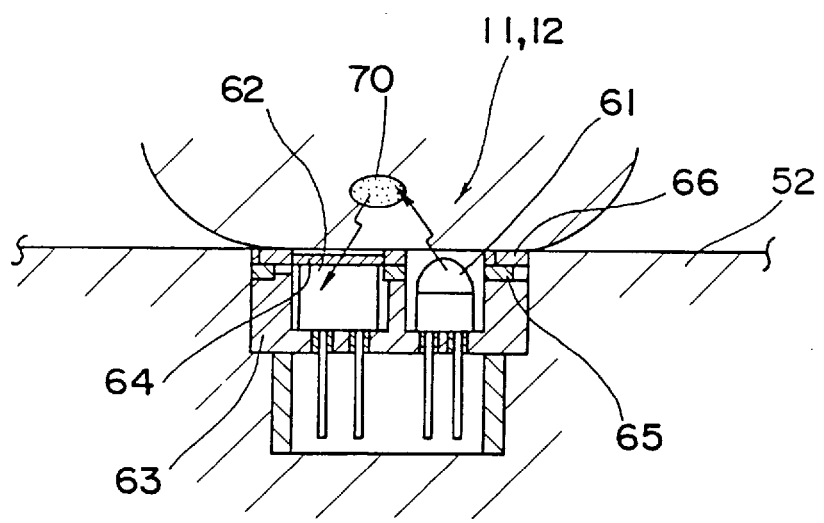
FIG. 6 is a schematic cross-sectional view of an infrared type heartbeat sensor.

Specifically, in the infrared type heartbeat sensors 11 and 12, as shown in FIG. 6, a resin-made housing 63 is embedded in the wheel 52 of the steering wheel 33 and the infrared light emitting diode 61 and the phototransistor 62 are disposed in the housing 63. The phototransistor 62 includes a visible light cut filter 64 on an outer surface and a cover 66 is provided through a rubber 65 on an outer surface of the housing other than the infrared light emitting diode 61 and the phototransistor 62.

Figure 7:
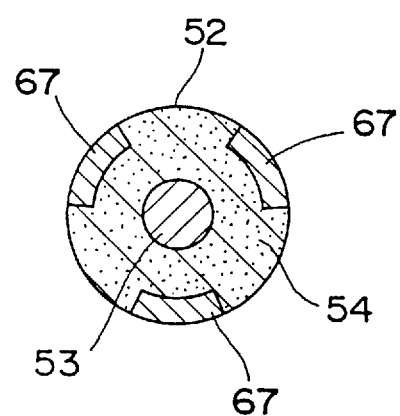
FIG. 7 is a schematic cross-sectional view of a wheel of the steering wheel.

The potential type heartbeat sensor 16, as shown in FIGS. 4 and 5, includes a pair of electrodes 67 and 68 disposed along the peripheral direction on both sides of the wheel 52 of the steering wheel 33. That is, the wheel 52 of the steering wheel 33, as shown in FIG. 7, is formed of a foamed polyurethane 54 around the periphery of a small-diameter rim 53. Three recesses are formed in the peripheral direction of the steering wheel 33 on the surface of the foamed polyurethane 54, where the individual electrodes 67 and 68 are disposed.

Further, a controller 69 is disposed in the hub 51 of the steering wheel 33, which is connected to the infrared light emitting diode 61 and the phototransistor 62 of the infrared type heartbeat sensors 11 and 12 and the pair of electrodes 67 and 68 of the potential type heartbeat sensor 16.

In the present embodiment, when the driver grips the steering wheel 33 naturally, the flats of the right and left hands contact the pair of electrodes 67 and 68 of the potential type heartbeat sensor 16, and the thumbs contact the infrared light emitting diode 61 and the phototransistor 62 of the infrared type heartbeat sensors 11 and 12. The infrared type heartbeat sensors 11 and 12, as shown in FIG. 6, detect pulsating of blood flowing in vessels when is infrared light emitted from the infrared light emitting diode 61 is reflected by hemoglobin in the vessel 70 and incident on the phototransistor 61. Further, the potential type heartbeat sensor 16 detects a pulsed blood potential difference between both hands of the driver from the pair of electrodes 67 and 68, thereby detecting the heartbeat.

The mounting structure of the infrared type heartbeat sensors 11 and 12 and the potential type heartbeat sensor 16 are not limited to the above embodiment. Other embodiments are shown in FIGS. 8 to 11.

Figure 8:
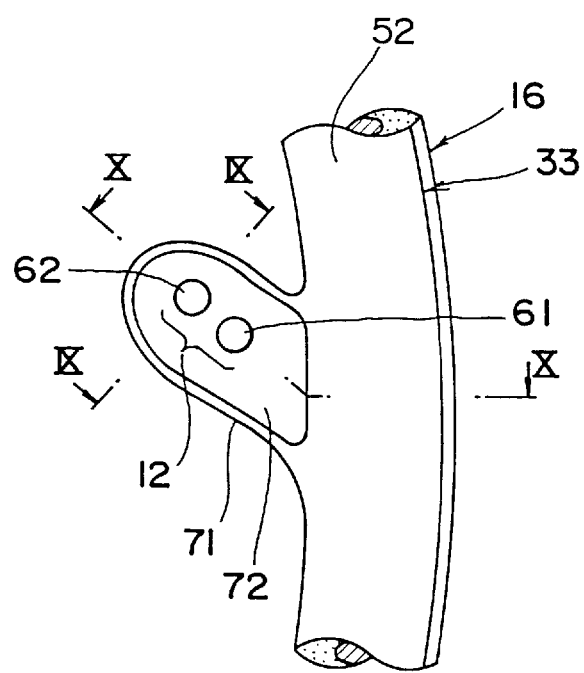
FIG. 8 is a schematic view of the steering wheel showing other infrared type heartbeat sensor and potential type heartbeat sensor.
Figure 9:
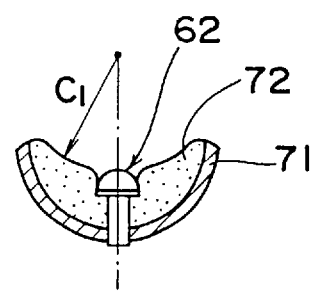
FIG. 9 is a schematic cross-sectional view taken along line IX—IX in FIG. 8.
Figure 10:
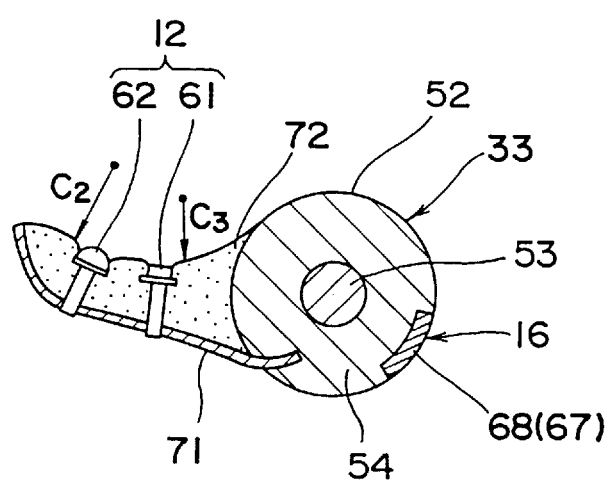
FIG. 10 is a schematic cross-sectional view taken along line X—X in FIG. 9.

As shown in FIG. 8, the infrared type heartbeat sensors 11 and 12 include the infrared light emitting diode 61 and the phototransistor 62, which are disposed at two positions where the driver naturally grips the steering wheel 33 with right and left hands. As shown in FIGS. 9 and 10, in the wheel 52 of the steering wheel 33, a resin-made cover 71 is mounted projecting inward at a predetermined position in the peripheral direction, and the cover 71 is provided with the infrared light emitting diode 61 and the phototransistor 62 disposed side by side. The cover 71 is filled with an elastic member 72 such as silicone, thereby holding the infrared light emitting diode 61 and the phototransistor 62.

Figure 11:
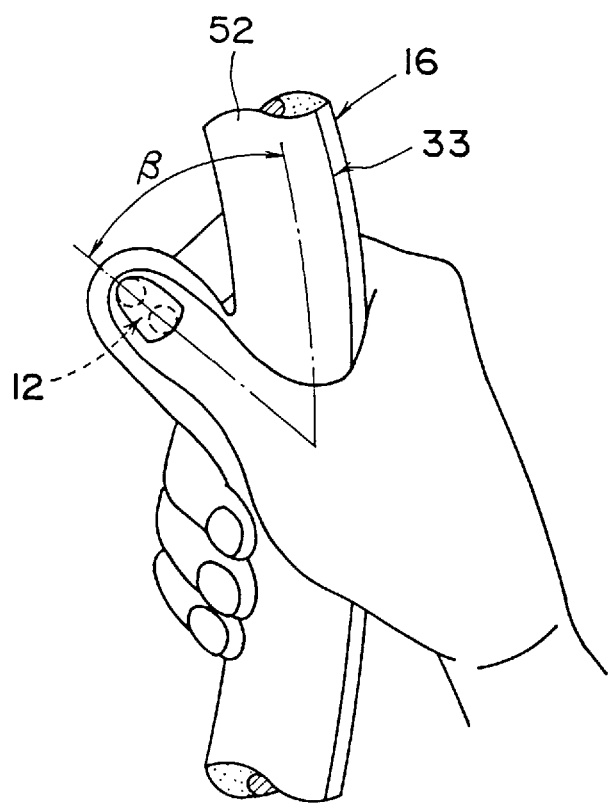
FIG. 11 is a schematic view showing grip condition of the steering wheel by hands.

In the elastic member 72 inside the cover 71, contact portions which contact with the thumbs are formed with predetermined curvatures C1, C2, and C3 corresponding to the shapes of the contacting thumbs, to achieve close contact with each other. Further, the infrared light emitting diode 61 and the phototransistor 62, shown in FIG. 11, are arranged at an angle b between the thumb direction and the peripheral direction of the steering wheel 33 when the driver grips the steering wheel 33. While the embodiment shows the case of the right hand, the arrangement is similar for the left hand.

The potential type heartbeat sensor 16, as shown in FIGS. 8 and 10, is provided with a pair of electrodes 67 and 68 along the peripheral direction on both sides of the wheel 52 of the steering wheel 33.

In the present embodiment, the infrared type heartbeat sensors 11 and 12 are disposed at positions contacting with the thumbs when the driver grips the steering wheel 33 naturally and the elastic member 72 has a curvature corresponding to the shapes of the driver thumbs are provided on the surfaces contacting with the thumbs. As a result the infrared heartbeat sensors 11 and 12 closely fit the driver's thumbs and are less affected by external light, thereby achieving close contact of the driver's thumbs with the heartbeat sensors 11 and 12. Further, in the present embodiment, since variations in pressing force of the fingers can be absorbed by the elastic member 72, a disturbance of blood flow under the skin is prevented. As a result, signals detected by the heartbeat sensors 11 and 12 are amplified by an amplified signal conversion unit (not shown), the heartbeat rate is precisely detected from the signals, and an abnormality according to the rhythm pattern can be detected with high precision.

Figure 12:
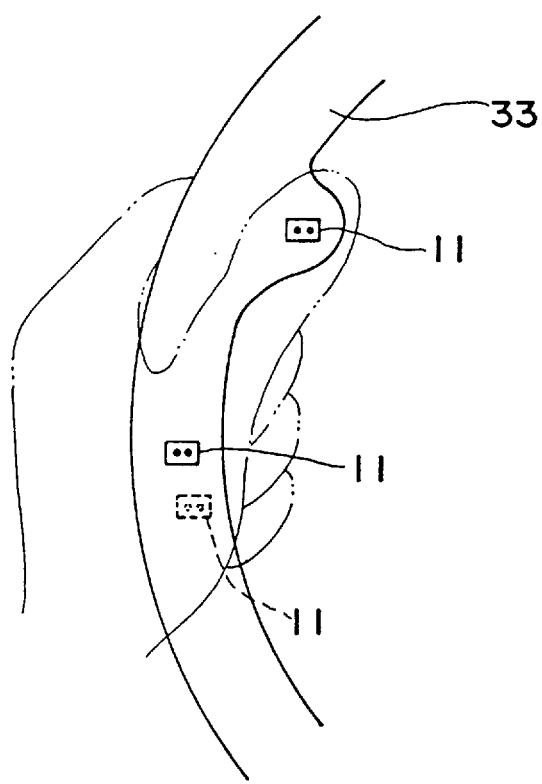
FIG. 12 is a schematic view of the steering wheel showing another infrared type heartbeat sensor.
Figure 13:
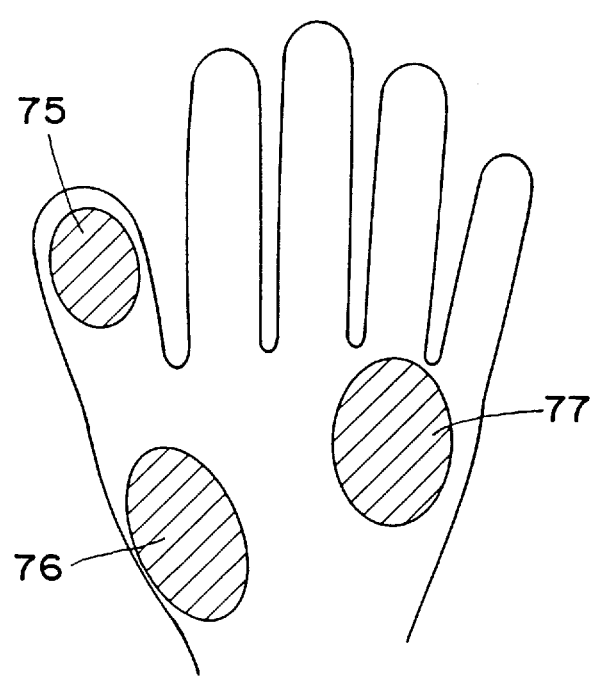
FIG. 13 is a schematic view showing a portion having large amounts of blood flow in the hand.

Further, another embodiment in terms of the mounting structure of the infrared type heartbeat sensors is shown in FIGS. 12 and 13. In this embodiment, as shown in FIG. 12, three units of the infrared type heartbeat sensors 11 and 12 are provided on one of right and left sides of the steering wheel 33. As shown in FIG. 13, blood flow rates are large at a first portion 75 of the thumb, and a second portion 76 and a third portion 77 of the palm. The infrared type heartbeat sensors 11 are disposed at positions of the steering wheel 33 corresponding to the first through third positions 75, 76, and 77.

Therefore, detection errors caused by slight differences in gripping positions due to individual driver differences can be eliminated by the three infrared type heartbeat sensors 11, thereby accurately detecting the heartbeat rate of the driver.

Figure 14:
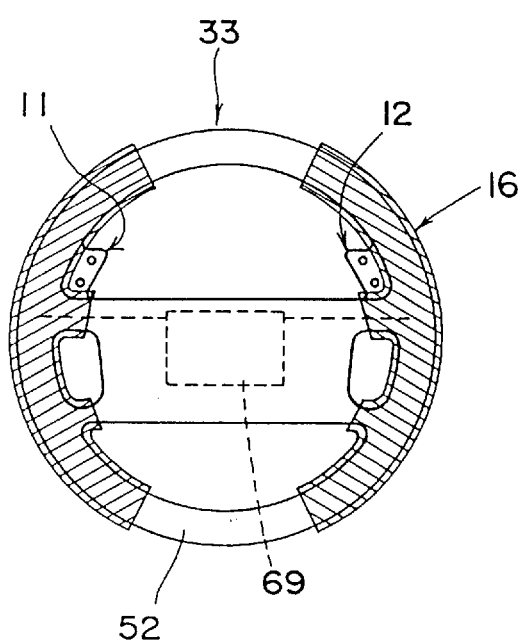
FIG. 14 is a schematic front view of the steering wheel showing another potential type heartbeat sensor.

Further, another embodiment of the potential type heartbeat sensor is shown in FIG. 14. As shown in FIG. 14, the potential type heartbeat sensors 16 are disposed on right and left sides of the steering wheel 33 so that a cover is formed by electrodes to cover the wheel 52. This arrangement also provides a better fit than the electrode embedding type.

The heartbeat processing means 13 and 14 calculate the driver's heartbeat rate according to detection signals from the infrared heartbeat sensors 11 and 12, and similarly the heartbeat processing means 17 calculates the driver's heartbeat rate according to a detection signal from the potential heartbeat sensor 16. The calculations performed by the heartbeat processing means 13, 14, and 17 are basically the same, in which abnormal detection signals are appropriately corrected to calculate a heartbeat pulse interval (hereinafter referred to as "pulse interval") and the heartbeat rate corresponding to the pulse interval.

Figure 15:
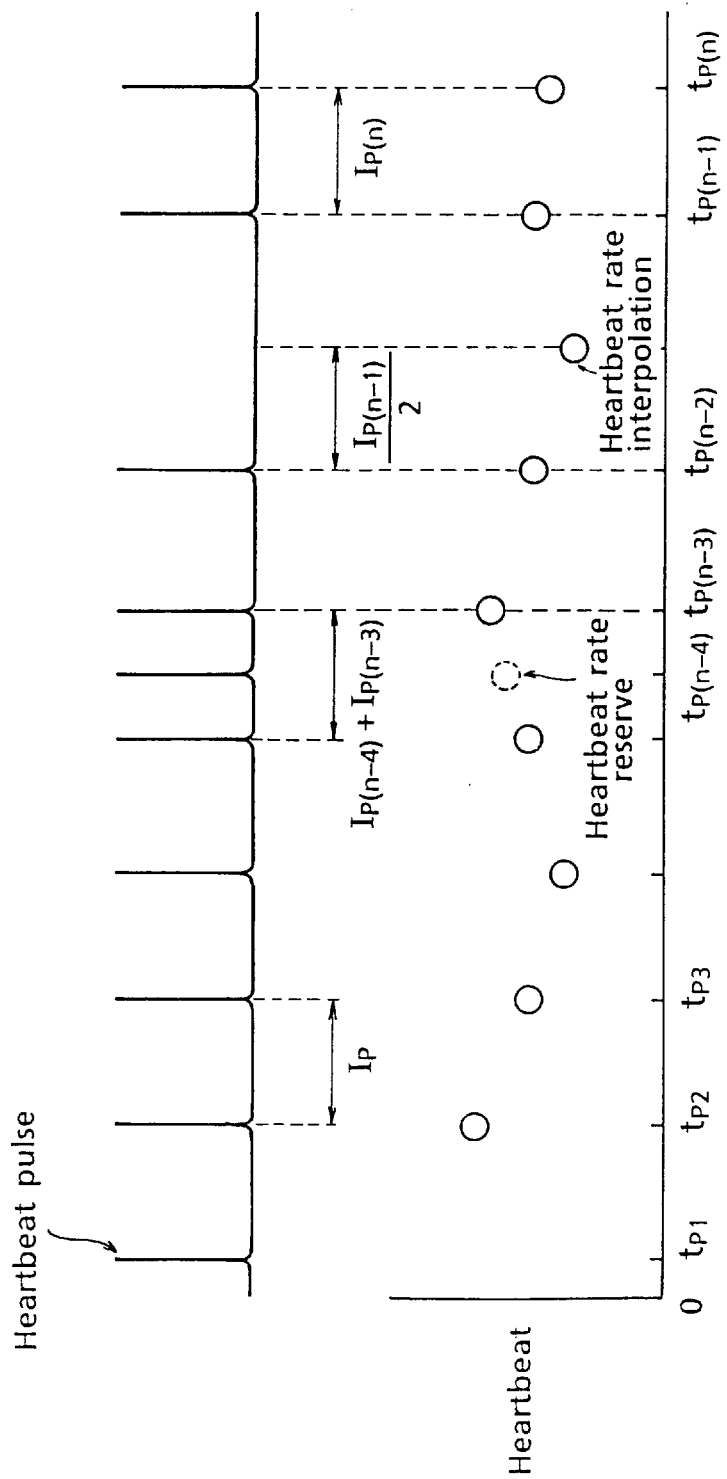
FIG. 15 is a schematic view showing a relationship between heartbeat pulse from a heartbeat sensor and heartbeat rate data calculated by heartbeat processing means.

FIG. 15 shows a relationship between heartbeat data calculated by the heartbeat processing means 13, 14, and 17 and the heartbeat pulses detected by the heartbeat sensors, for example, when the pulse interval suddenly becomes shorter than the previously measured pulse interval, the heartbeat calculation according to the pulse interval at that time is temporality reserved, when the sum of the next measured pulse interval and the previous pulse interval is almost the same as the previous pulse interval, the previous heartbeat pulse information is determined to be due to noise, and the previous heartbeat data is canceled. For example, pulse intervals $I_{P(n-4)}$ and $I_{P(n-3)}$ at time $t_{P(n-4)}$ and a following time $t_{P(n-3)}$ are abnormally shorter than a past pulse interval $I_P$. As a result, the heartbeat rate calculated at the time $t_{P(n-4)}$ is reserved and, when the sum of the two pulse intervals $I_{P(n-4)}$ and $I_{P(n-3)}$ is almost the same as the past pulse interval, the heartbeat pulse at time $t_{P(n-3)}$ is determined to be due to noise, and the heartbeat data at time $t_{P(n-4)}$ is canceled. Further, when the pulse interval suddenly becomes longer, when the next measured pulse interval is almost the same as the past pulse interval, half of the time of the previous pulse interval is added to the time at which the pulse interval before the previous pulse interval was calculated to interpolate heartbeat data at that time. For example, when the pulse interval at time $t_{P(n-1)}$ is abnormally longer than the past pulse interval $I_P$, when a pulse interval $I_{P(n)}$ at time $t_{P(n)}$ at which the next heartbeat pulse is detected is almost the same as the past pulse interval $I_P$, it is determined that a normal heartbeat pulse could not be detected between the previous time and the time before previous time, and half of the time of the previous pulse interval $I_{P(n-1)}$ is added to time $t_{P(n-2)}$ at which the heartbeat pulse before the previous time was detected to calculate a heartbeat rate at this point of time.

Figure 16:
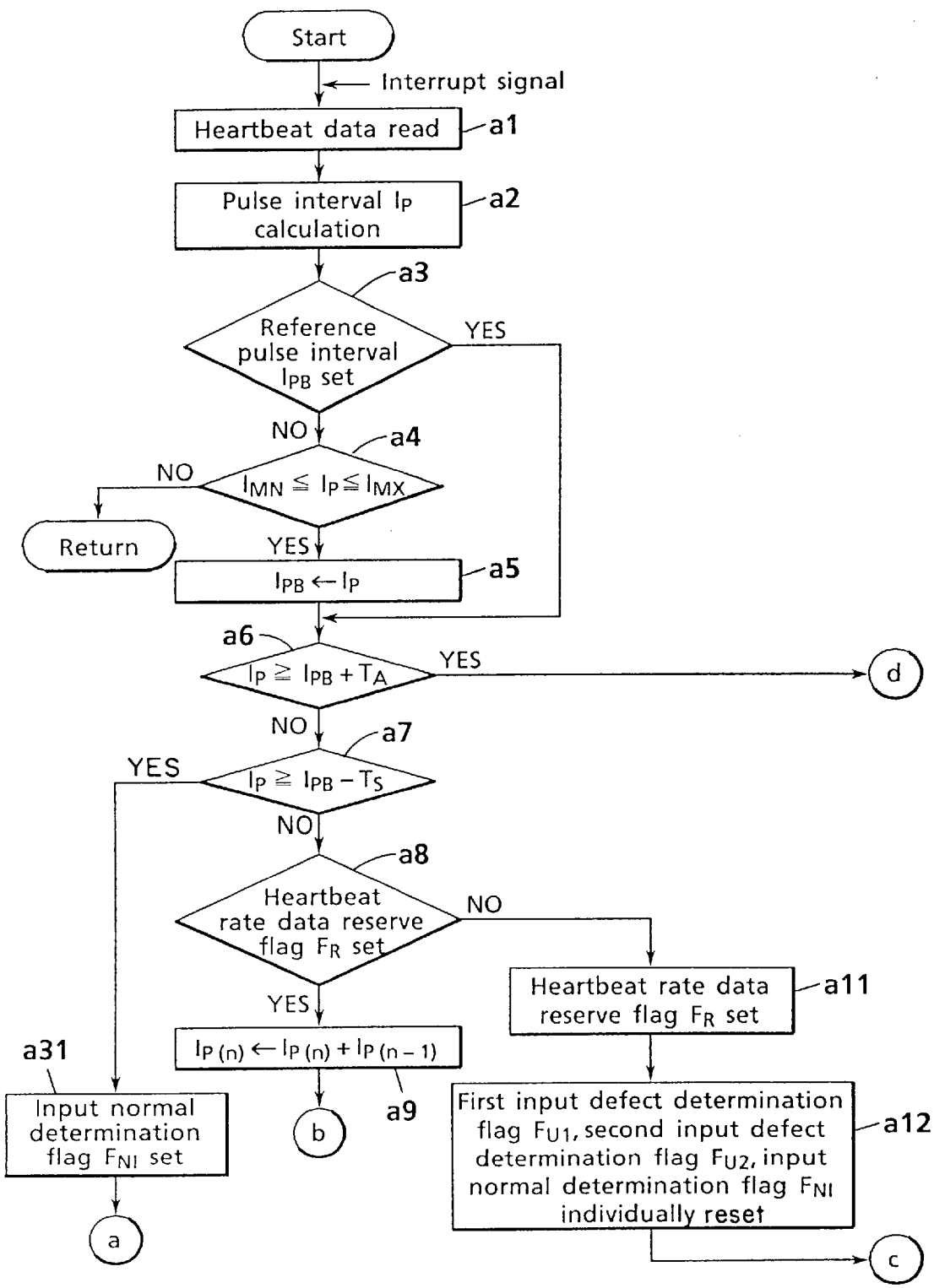
FIG. 16 is a flow chart showing processing performed by the heartbeat processing means of the embodiment along with FIGS. 17 and 18.
Figure 17:
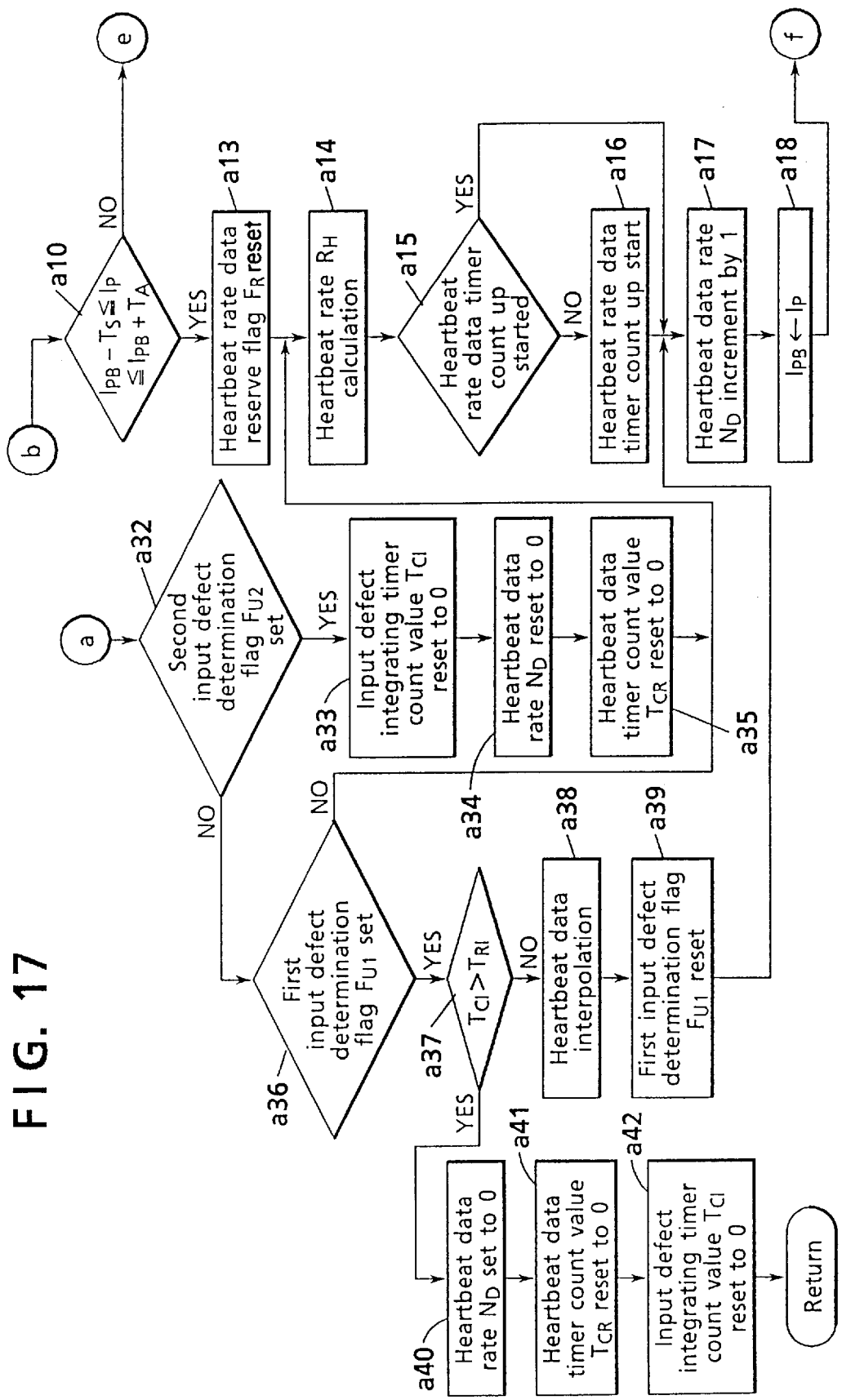
FIG. 17 is a flow chart showing processing performed by the heartbeat processing means of the embodiment along with FIGS. 16 and 18.
Figure 18:
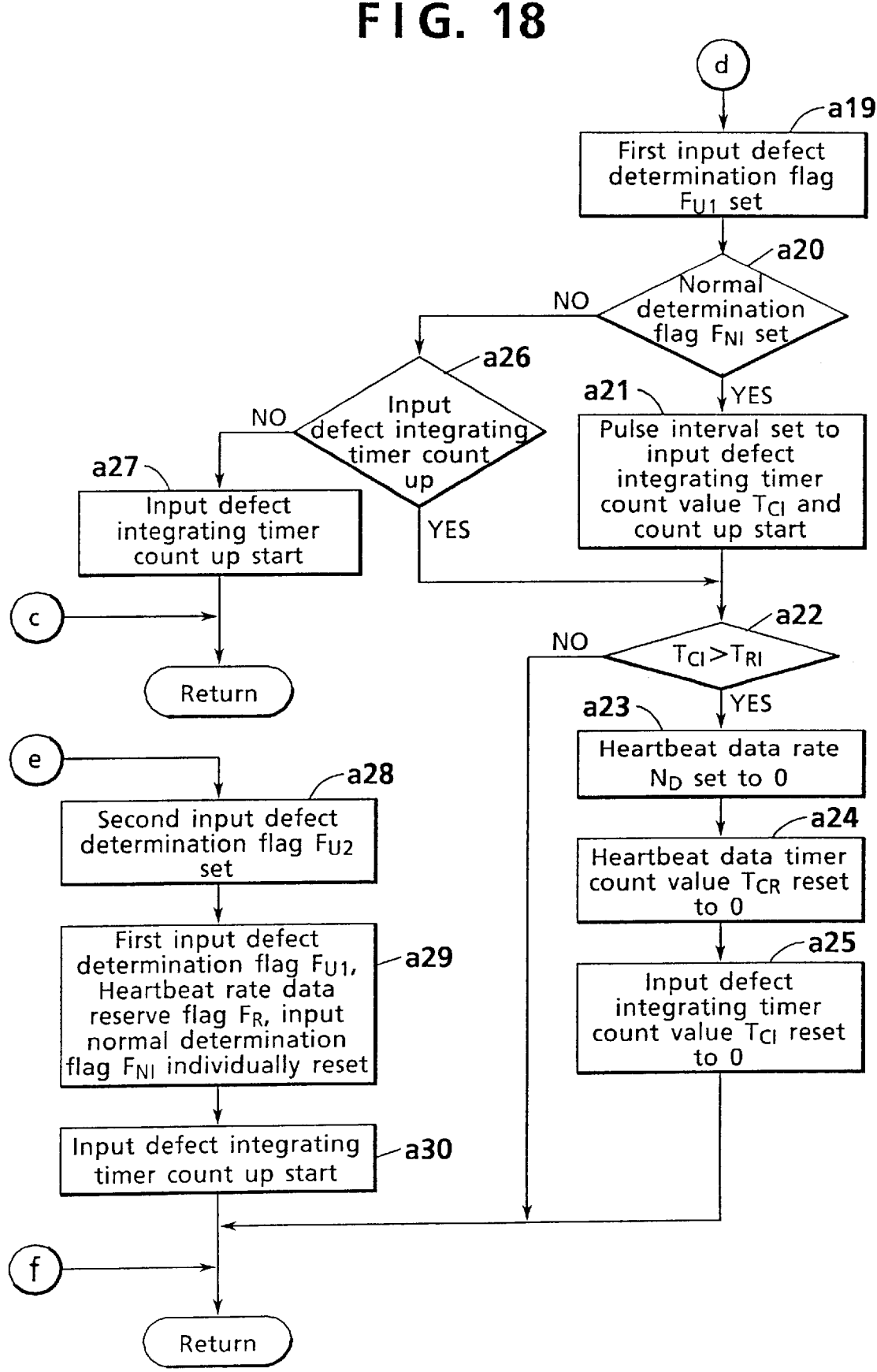
FIG. 18 is a flow chart showing processing performed by the heartbeat processing means of the embodiment along with FIGS. 16 and 17.

The processing flow of the heartbeat processing means 13, 14, and 17 is shown in FIGS. 16 to 18. Processing by the heartbeat processing means 13, 14, and 17 in the present embodiment is made in a predetermined period, for example, every time at an interrupt signal of every 15 msec. First, in step a1, the detection time $t_p$ of a heartbeat pulse detected by the heartbeat sensors 11, 12, and 16 is read, in step a2, the present pulse detection time $t_{P(n)}$ is subtracted by the previous pulse detection time $t_{P(n-1)}$, and the present pulse interval $I_{P(n)}$ according to the following equation:

$$I_{P(n)}=t_{P(n)}-t_{P(n-1)}.$$

Then, it is determined in step a3 whether or not a pulse interval reference value $I_{PB}$ is set, however, since the pulse interval reference value $I_{PB}$ is not set at the beginning, processing proceeds to step a4, where a determination is made as to whether or not the pulse interval $I_{P(n)}$ is between a preset minimum pulse interval $I_{MN}$, for example, 600 msec, and a maximum pulse interval $I_{MX}$, for example, 1200 msec.

When it is determined in step a4 that the pulse interval $I_{P(n)}$ is not between the minimum pulse interval $I_{MN}$ and the maximum pulse interval $I_{MX}$, that is, the pulse interval $I_{P(n)}$ calculated in step a2 is abnormal, processing returns to step a1 after the above-described interrupt signal of a predetermined period. When it is determined in step a4 that the pulse interval $I_{P(n)}$ is between the minimum pulse interval $I_{MN}$ and the maximum pulse interval $I_{MX}$, that is, the pulse interval $I_{P(n)}$ calculated in step a2 is a normal value, the pulse interval $I_{P(n)}$ calculated in step a2 is adopted as the reference pulse interval $I_{PB}$ in step a5, and a determination is made in step a6 as to whether or not the present pulse interval $I_{P(n)}$ is longer than the sum of the reference pulse interval $I_{PB}$ and a preset additional time $T_A$, for example, 250 msec. Also, when it is determined in step a3 that the reference pulse interval $I_{PB}$ is set, processing proceeds to step a6.

When it is determined in step a6 that the present pulse interval $I_{P(n)}$ is shorter than the sum of the reference pulse interval $I_{PB}$ and the preset additional time $T_A$, that is, the value of the presently calculated pulse interval $I_{P(n)}$ is normal, a determination is made in step a7 as to whether or not the pulse interval $I_{P(n)}$ is shorter than a value of the reference pulse interval $I_{PB}$ subtracted by a preset subtraction time $T_S$, for example, 250 msec, and when it is determined in step a7 that the pulse interval $I_{P(n)}$ is less than the reference pulse interval $I_{PB}$ subtracted by the preset subtraction time $T_S$, that is, the presently calculated pulse interval $I_{P(n)}$ could be abnormal, a determination is made in step a8 as to whether or not a heartbeat data reserve flag $F_R$, which will be described later, is set.

When it is determined in step a8 that the heartbeat data reserve flag $F_R$ is set, that is the previous determination is reserved because the previously calculated pulse interval $I_{P(n-1)}$ could be abnormal, processing proceeds to step a9, where the present pulse interval $I_{P(n)}$ is corrected to the sum of the present pulse interval $I_{P(n)}$ and the previous pulse interval $I_{P(n-1)}$, and a determination is made again in step a10 as to whether or not the corrected present pulse interval $I_{P(n)}$ is more than the reference pulse interval $I_{PB}$ subtracted by the subtraction time $T_S$ and less than the sum of the reference pulse interval $I_{PB}$ and the above additional time $T_A$. When it is determined in step a8 that the heartbeat data reserve flag $F_R$ is not set, that is, the previously calculated pulse interval $I_{P(n-1)}$ is normal and the present pulse interval $I_{P(n)}$ is abnormal, processing proceeds to step a11, where the heartbeat data reserve flag $F_R$ is set and, in step a12, a first input defect determination flag $F_{U1}$, a second input defect determination flag $F_{U2}$, and an input normal determination flag $F_{NI}$, which will be described later, are individually reset, and processing returns to step a1 following the next interrupt signal.

When it is determined in step a10 that the pulse interval $I_{P(n)}$ set in step a9 is more than the value of the reference pulse interval $I_{PB}$ subtracted by the preset subtraction time $T_S$ and less than the sum of the reference pulse interval $I_{PB}$ and the preset additional time $T_A$, that is, the previous pulse interval $I_{P(n-1)}$ is abnormal, processing proceeds to step a13, where the heartbeat data reserve flag $F_R$ is reset. A present heartbeat rate $R_{H(n)}$ is calculated in step a14 according to the pulse interval $I_{P(n)}$ corrected in step a9, and a determination is made in step a15 as to whether or not the heartbeat data timer has begun counting up, using the following equation:

$$R_{H(n)}=60/I_{P(n)}.$$

When it is determined in step a15 that the heartbeat data timer has not begun counting up, counting up of the heartbeat data timer begins in step a16, the heartbeat data number $N_D$ is incremented by one in step a17, the pulse interval $I_{P(n)}$ set in step a9 is adopted as a new reference pulse interval $I_{PB}$ in step a18, and processing returns to step a1 following the above-described interrupt signal of the predetermined period.

On the other hand, when it is determined in step a6 that the pulse interval $I_{P(n)}$ is more than the sum of the reference pulse interval $I_{PB}$ and the preset additional time $T_A$, that is, a heartbeat pulse was expected between the previous time and the present time, processing proceeds to step a19, where the first input defect determination flag $F_{U1}$ is set, a determination is made in step a20 as to whether or not the input normal determination flag $F_{NI}$ described later is set, that is, the previous input is normal, processing proceeds to step a21, where the previously set pulse interval $I_{P(n)}$ is set as an initial time of an input defect integrating timer, from which counting up is begun, and a determination is made in step a22 as to whether or not a count value $T_{CI}$ by the input defect integrating timer is longer than a preset time $T_{RI}$.

When it is determined in step a22 that the count value $T_{CI}$ of the input defect integrating timer is less than the above preset time $T_{RI}$, processing proceeds to step a1 after the above-described predetermined period interrupt signal. Further, when it is determined in step a22 that the count value $T_{CI}$ of the input defect integrating timer exceeds the preset time $T_{RI}$, that is, the heartbeat pulse data read in step a1 is due to continuous noise, the heartbeat data number ND is set to 0 in step a23, the count value $T_{CR}$ of the heartbeat data timer is reset to 0 in step a24, counting Up of the input defect integrating timer is reset in step a25, and processing returns to step a1 following the predetermined period interrupt signal.

Further, when it is determined in step a20 that the input normal determination flag $F_{NI}$ is not set, that is, the previous input is abnormal, processing proceeds to step a26, where a determination is made as to whether or not the input defect integrating timer has begun counting up, when it is determined in step a26 that the input defect integrating timer has begun counting up, processing proceeds to the above step a22. To the contrary, when it is determined in step a26 that counting up has not begun by the input defect integrating timer, counting up of the input defect integrating timer begins in step a27, and processing returns to step a1 following the predetermined period interrupt signal.

When it is determined in step a10 that the pulse interval $I_{P(n)}$ set in step a9 is shorter than the value of the reference pulse interval $I_{PB}$ subtracted by the subtraction time $T_S$, or the pulse interval $I_{P(n)}$ is longer than the sum of the reference pulse interval $I_{PB}$ and the additional time $T_A$, that is, also the presently corrected pulse interval $I_{P(n)}$ is also abnormal, processing proceeds to step a28, where the second input defect determination flag $F_{U2}$ is set, and the first input defect determination flag $F_{U1}$, the input normal determination flag $F_{NI}$, and the heartbeat data reserve flag $F_R$ are individually reset in step a29, counting up of the input defect integrating timer begins in step a30, and processing returns to step a1 following the predetermined period interrupt signal.

Further, when it is determined in step a7 that the pulse interval $I_{P(n)}$ is longer than the value of the reference pulse interval $I_{PB}$ subtracted by the subtraction time $T_S$, that is, the presently calculated pulse interval $I_{P(n)}$ is normal, processing proceeds to step a31, where the normal input determination flag $F_{NI}$ used in the determination step of a20 is set, and a determination is made in step a32 as to whether or not the second input defect determination flag $F_{U2}$ is set. When it is determined in step a32 that the second input defect determination flag $F_{U2}$ is set, that is, abnormal heartbeat pulses are detected in two successive times, processing proceeds to step a33, where the count value $T_{CI}$ of the input defect integrating timer is reset to 0, the heartbeat data number $N_D$ is reset to 0 in step a34, the count value $T_{CR}$ of the heartbeat data timer is reset to 0 in step a35, and processing proceeds to step a14.

On the other hand, when it is determined in step a32 that the second input defect determination flag $F_{U2}$ is not set, processing proceeds to step a36, where a determination is made as to whether or not the first input defect determination flag $F_{U1}$ is set. When it is determined in step a36 that the first input defect determination flag $F_{U1}$ is set, that is, the previously calculated pulse interval $I_{P(n-1)}$ is too long compared to that previous calculations, processing proceeds to step a37, where a determination is made as to whether or not the count value $T_{CI}$ of the input defect integrating timer is greater than the preset time $T_{RI}$. When it is determined in step a36 that the first input defect determination flag $F_{U1}$ is not set, processing returns to step a14.

When it is expected in step a37 that the count value $T_{CI}$ of the input defect integrating timer is longer than the preset time $T_{RI}$, that is, there was an undetected heartbeat pulse between the previous time and the time before previous time, a heartbeat data interpolation is made for the heartbeat pulse undetected between the previous time and the time before previous time, the first input defect determination flag $F_{U1}$ is reset in step a39, and processing returns to step a17.

When it is determined in step a37 that the count value $T_{CI}$ of the input defect integrating timer is longer than the preset time $T_{RI}$, that is, the previously calculated pulse interval $I_{P(n-1)}$ is abnormally long, since it is not a normal heartbeat pulse, processing proceeds to step a40, where the heartbeat data number $N_D$ is reset to 0, the count value $T_{CR}$ of the heartbeat data timer is reset to 0 in step a41, the count value $T_{CI}$ of the input defect integrating timer is reset to 0, and processing returns to step a1 following the predetermined period interrupt signal.

Heartbeat data calculated by these heartbeat processing means 13 and 14 should basically be the same but, when the heartbeat data differs for some reason, the signal selection means 15 adopts the one which outputs a greater heartbeat rate from the two heartbeat processing means 13 and 14 in view of control safety, and outputs it to the heartbeat processing means 18. Since the present embodiment employs two infrared heartbeat sensors 11 and 12, an exact heartbeat rate can be calculated even when the steering wheel 33 is gripped by only the right or left hand. In this case, it is natural to adopt the output from heartbeat processing means which outputs normal heartbeat data.

In the present embodiment, the heartbeat data processing means 18 calculates an average of heartbeat data of past four times (hereinafter referred to as "4-point running average heartbeat rate), because there are 3 or 4 heartbeats during a respiration of one time in a rest, considering periodical changes in heartbeat in association with the driver's respiration, to remove fluctuations in heartbeat rate due to the driver's respiration. Further, from the 4-point running average heartbeat rates of the present time, previous time, and the time before previous time, calculation is made as to whether it is a peak point heartbeat rate in which the 4-point running average heartbeat rate of the previous time changes from an increasing tendency to a decreasing tendency, or from a decreasing tendency to an increasing tendency. Then, a gradient of adjacent peak point heartbeat rate obtained by dividing a deviation of adjacent peak point heartbeat rates by the time interval is calculated, and an average of heartbeat rate data of past 10 times (hereinafter referred to as "10-point running average heartbeat rate") and a simple average of heartbeat rate for past 30 seconds (hereinafter referred to as "30-sec average heartbeat rate") are calculated.

Figure 19:
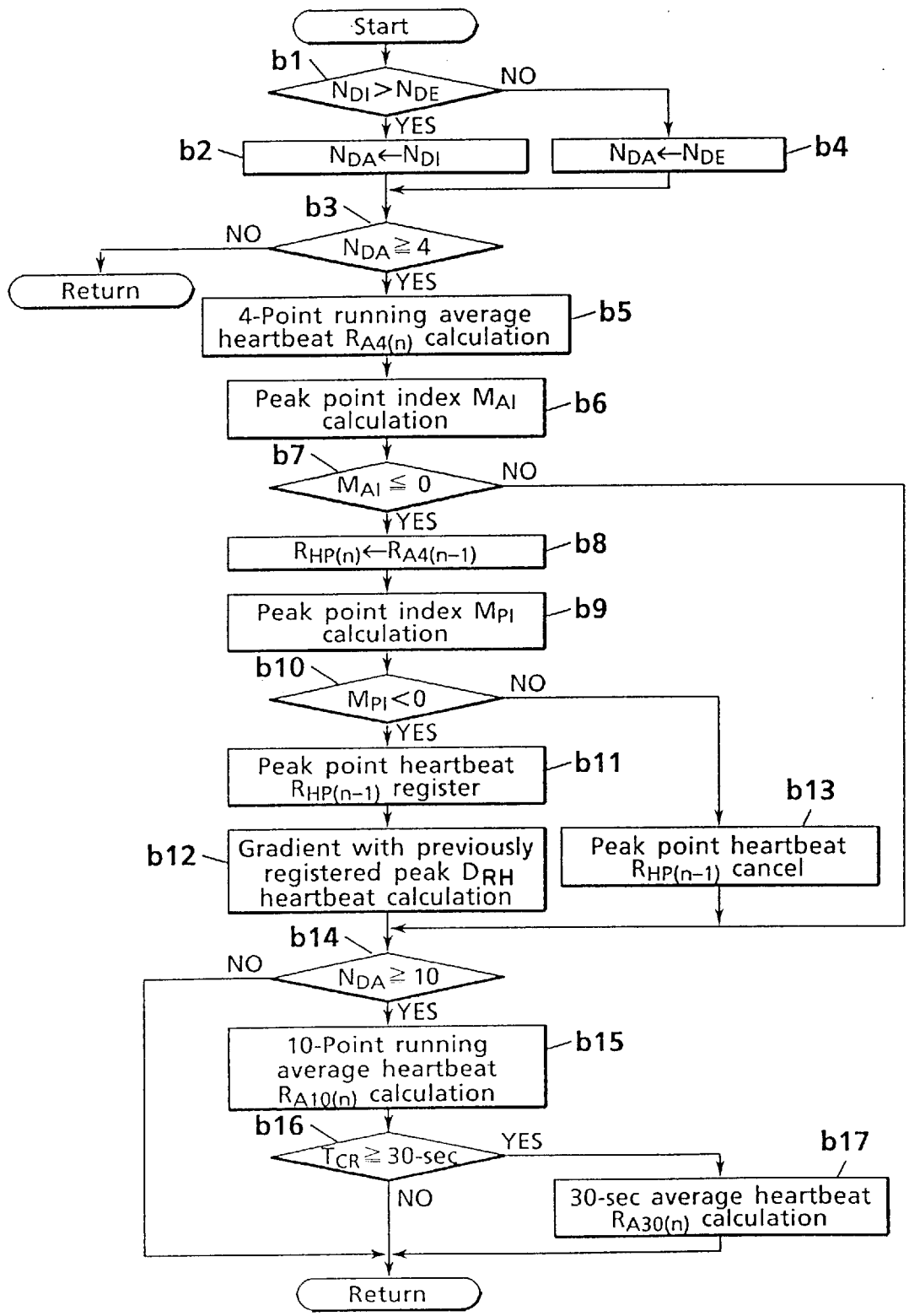
FIG. 19 is a flow chart showing processing performed by the heartbeat data processing means of the present embodiment.

Processing flow in the heartbeat data processing means 18 in the present embodiment is shown in FIG. 19. Specifically, a determination is made in step b1 as to whether or not the heartbeat data number $N_{DI}$ from the signal selection means 15 is more than the heartbeat data number NDE from the potential heartbeat sensor 16, and when it is determined in step b1 that the heartbeat data number $N_{DI}$ from the signal selection means 15 is more than the heartbeat data number NDE from the potential heartbeat sensor 16, processing proceeds to step b2, where the heartbeat data number $N_{DI}$ from one of the infrared heartbeat sensors 11 and 12 through the signal selection means 15 is adopted as an effective heartbeat data number $N_{DA}$, and a determination is made in step b3 as to whether or not the effective heartbeat data number $N_{DA}$ is more than 4 which is the number of data required for calculating a 4-point running average heartbeat rate $R_{A4}$. Further, when it is determined in step b1 that the heartbeat data number $N_{D1}$ from the signal selection means 15 is less than the heartbeat data number $N_{DE}$ from the potential heartbeat sensor 16, processing proceeds to step b4, where the heartbeat data number $N_{DE}$ from the potential heartbeat sensor 16 is adopted as the effective heartbeat data number $N_{DA}$, and then processing proceeds to step b3.

When it is determined in step b3 that the effective heartbeat data number $N_{DA}$ is 4 or more, a 4-point running average heartbeat rate $R_{A4(n)}$ is calculated in step b5, a peak point index $M_{A1}$ of the 4-point running average heartbeat rate $R_{A4}$ is calculated using the equation recited below in step b6, and then a determination is made in step b7 as to whether or not the peak point index $M_{A1}$ is 0 or less. When it is determined in step b3 that the effective heartbeat data number $N_{DA}$ is less than 4, since the 4-point running average heartbeat rate $R_{A4(n)}$ cannot be calculated in step b5, processing returns to step b1.

$$M_{AI}\{R_{A4(n)}-R_{A4(n-1)}\}\cdot\{R_{A4(n-1)}-R_{A4(n-2)}\}.$$

When it is determined in step b7 that the peak point index $M_{AI}$ is less than 0, that is, the values are the same only at the present time and the previous time, or the same only at the previous time and at the time before the previous time, or the previous 4-point running average heartbeat rate $R_{A4(n-1)}$ is greater than the present one and the previous one is greater than the 4-point running average heartbeat rate $R_{A4(n-2)}$ at the time before previous time, or the present one is greater than the previous 4-point running average heartbeat rate $R_{A4(n-1)}$ and the 4-point running average heartbeat rate $R_{A4(n-2)}$ at the time before previous time, processing proceeds to step b8, where the previous 4-point running average heartbeat rate $R_{A4(n-1)}$ is temporarily adopted as a peak point heartbeat rate $R_{HP(n)}$, a peak point index $M_{PI}$ of a peak point heartbeat rate $R_{HP}$ is calculated using the equation recited below, and a determination is made in step b10 as to whether or not the peak point index $M_{PI}$ is less than 0:

$$M_{P1}\{R_{HP(n)}-R_{HP(n-1)}\}\cdot\{R_{HP(n-1)}-R_{HP(n-2)}\}.$$

When it is determined in step b10 that the peak point index $M_{P1}$ is smaller than 0, that is, the previous peak point heartbeat rate $R_{HP(n-1)}$ is greater or smaller than the present peak point heartbeat rate $R_{HP(n)}$ and the peak point heartbeat rate $R_{HP(n-2)}$ at the time before the previous time, processing proceeds to step b11, where the previous peak point heartbeat rate $R_{HP(n-1)}$ is registered, a gradient $D_{RH}$ is obtained by dividing a difference between the previously registered peak point heartbeat rate $R_{HP(n-2)}$ and the presently registered peak point heartbeat rate $R_{HP(n-1)}$ by this time is calculated in step b12, and a determination is made in step b14 as to whether or not the effective heartbeat data number $N_{DA}$ is 10 or more which is the number required for calculating a 10-point running average heartbeat rate $R_{A10}$. That is, when it is determined in step b10 that the peak point index $M_{PI}$ is 0 or more, that is, the previous peak point heartbeat rate $R_{HP(n-1)}$ is the same as the present time or the time before the previous time, or the magnitudes of the peak point heartbeat rates $R_{HP}$ are in the order of present time, previous time, and the time before previous time, processing proceeds to step b13, where the previous peak point heartbeat rate $R_{HP(n-1)}$ is not registered but reset, and then processing proceeds to step b14. Also, when it is determined in step b7 that the peak point index $M_{AI}$ exceeds 0, that is, if the magnitudes of the peak point heartbeat rates $R_{HP}$ are in the order of present time, previous time, and the time before previous time, then the previous 4-point running average heartbeat rate $R_{A4(n-1)}$ is not a peak point heartbeat rate, and processing proceeds to step b14.

When it is determined in step b14 that the effective heartbeat data number $N_{DA}$ is 10 or more, the 10-point running average heartbeat rate $R_{A10(n)}$ is calculated in step b15, and a determination is made in step b16 as to whether or not the count value $T_{CR}$ of the heartbeat timer is 30 seconds or more. When it is determined in step b14 that the effective heartbeat data number $N_{DA}$ is less than 10, since the 10-point running average heartbeat rate $R_{A10(n)}$ cannot be calculated in step b15, the processing returns to step b1.

When it is determined in step b16 that the count value $T_{CR}$ of the heartbeat data timer is 30 seconds or more, the 30-sec average heartbeat rate $R_{A30(n)}$ is calculated in step b17, and processing returns to step b1. When it is determined that the counter value $T_{CR}$ of the heartbeat data timer is less than 30 seconds, that is, the 30-sec average heartbeat rate $R_{A30(n)}$ cannot be calculated, the processing returns again to step b1.

The heartbeat awareness determination means 19 determines whether a variation in a heartbeat rate calculated by the heartbeat data processing means 18 is stable, that is, a variation width of the 4-point running average heartbeat rate within 30 seconds falls within 2, for example, and represents an area of stable awareness of the driver as shown in FIG. 3(4), the 30-sec average heartbeat rate $R_{A30}$ in the area of stable awareness calculated as a reference heartbeat rate and, when the peak point heartbeat rate $R_{HP}$ calculated by the heartbeat data processing means 18 is slightly smaller than the reference heartbeat rate after the driver is determined to be in the area of stable awareness, the driver is determined to be in a transition area in FIG. 3(5), and then the reference heartbeat rate and the present heartbeat data of the driver are compared to determine the awareness of the driver, setting a warning level corresponding to the driver's level of awareness.

Figure 20:
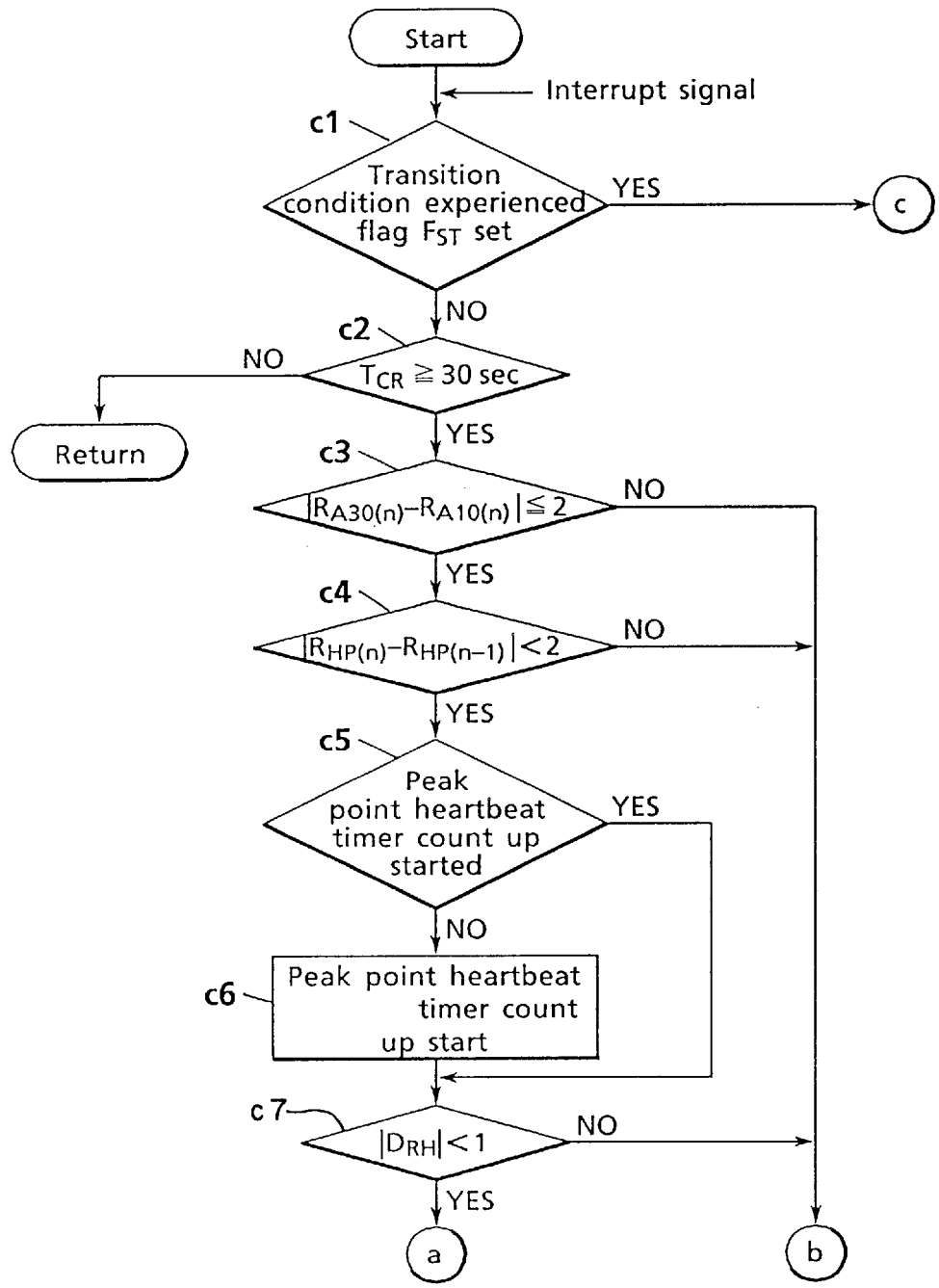
FIG. 20 is a flow chart showing processing performed by the heartbeat awareness determination means of the present embodiment along with FIGS. 21 and 22.
Figure 21:
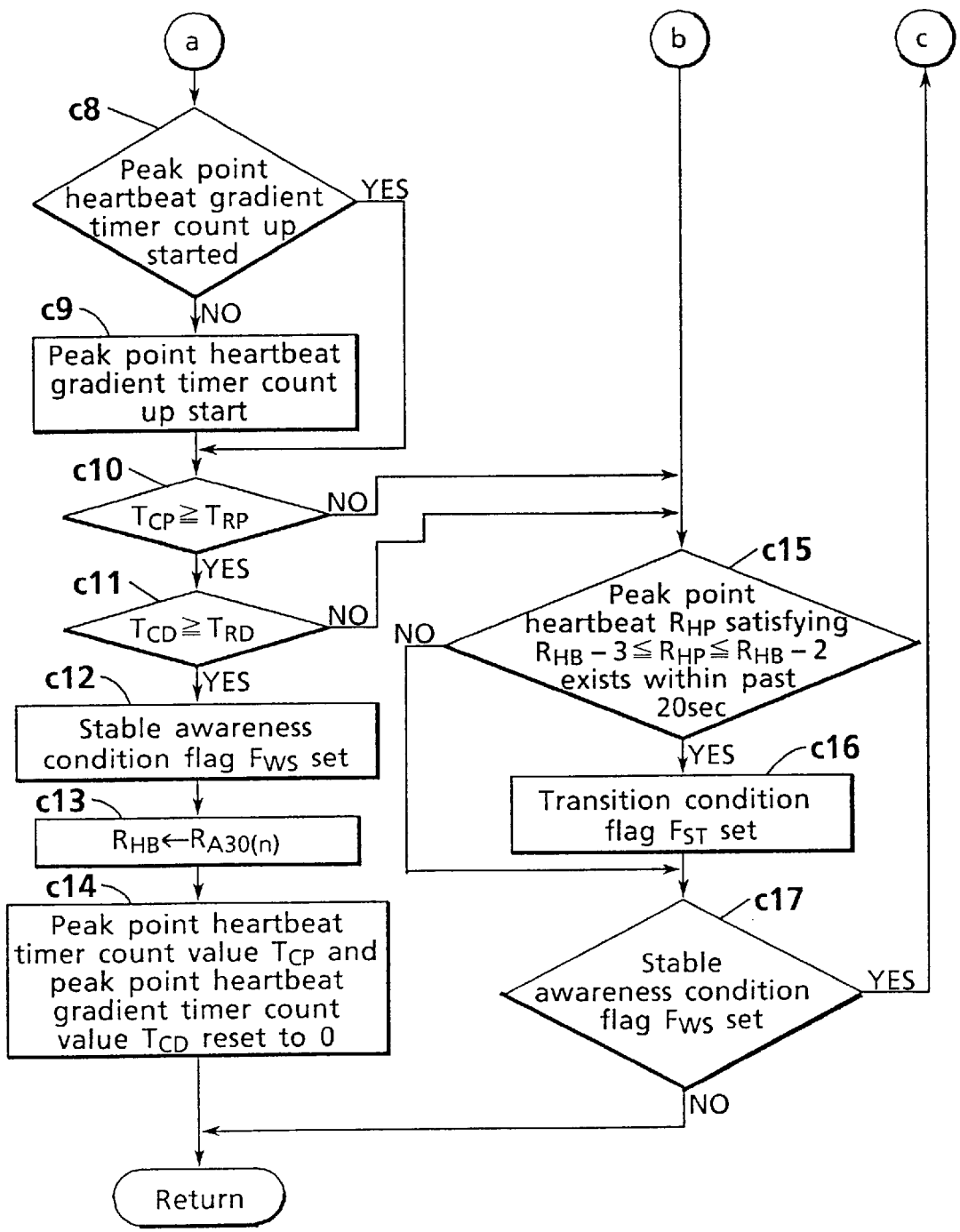
FIG. 21 is a flow chart showing processing performed by the heartbeat awareness determination means of the present embodiment along with FIGS. 20 and 22.
Figure 22:
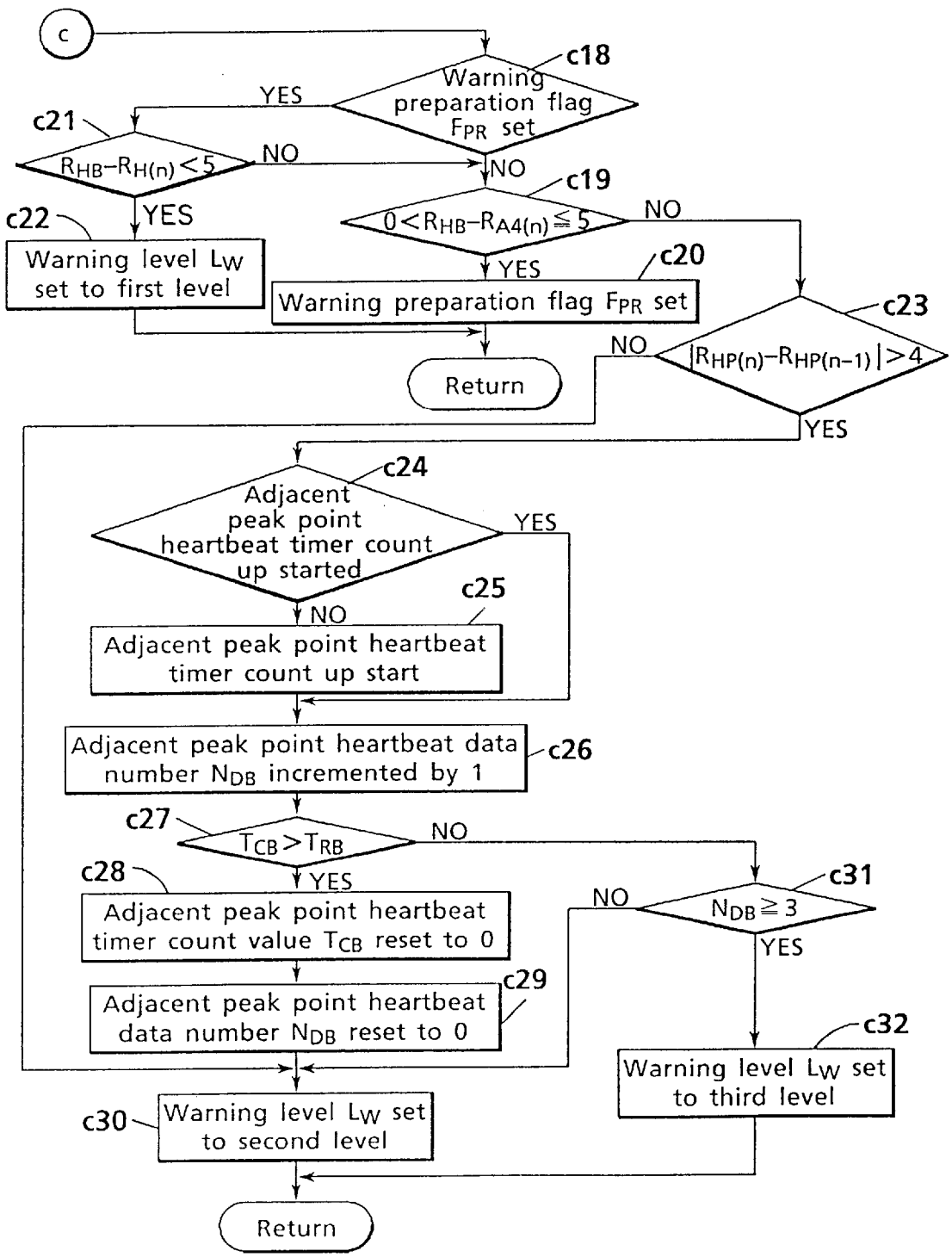
FIG. 22 is a flow chart showing processing performed by the heartbeat awareness determination means of the present embodiment along with FIGS. 20 and 21.

The processing flow of the heartbeat awareness determination means 19 in the present embodiment is shown in FIGS. 20 to 22. Specifically, in the present embodiment, processing by the heartbeat awareness determination means 19 is carried out in a predetermined period, for example, at every interrupt signal of 15 msec. First, a determination is made in step c1 as to whether or not a transition condition experienced flag $F_{ST}$ is set, however, since the transition condition experienced flag $F_{ST}$ is not set at the beginning, processing proceeds to step c2, where a determination is made in step c2 as to whether or not the count value $T_{CR}$ of the heartbeat data timer is 30 seconds or more. When it is determined in step c2 that the count value $T_{CR}$ of the heartbeat data timer is 30 seconds or more, that is, the heartbeat data is normal over a period of 30 seconds or more, the processing proceeds to step c3, where a determination is made as to whether or not an absolute value of the 30-sec average heartbeat rate $R_{A30(n)}$ subtracted by the 10-point running average heartbeat rate $R_{A10(n)}$ is 2 or less. When it is determined in step c2 that the count value $T_{CR}$ of the heartbeat data timer is shorter than 30 seconds, that is, the 10-point running average heartbeat rate $R_{A10(n)}$ cannot be calculated, the processing returns to step c1 and step c1 is repeated according to the next interrupt signal.

When it is determined in step c3 that the absolute value of the 30-sec average heartbeat rate $R_{A30(n)}$ subtracted by the 10-point running average heartbeat rate $R_{A10(n)}$ is 2 or less, that is, the heartbeat rate of the driver has almost no variation, a determination is made in step c4 as to whether or not the present peak point heartbeat rate $R_{HP(n)}$ subtracted by the previous peak point heartbeat rate $R_{HP(n-1)}$ is less than 2. When it is determined in step c4 that the absolute value of the present peak point heartbeat rate $R_{HP(n)}$ subtracted by the previous peak point heartbeat rate $R_{HP(n-1)}$ is less than 2, that is, a variation in the peak point heartbeat rate $R_{HP}$ is relatively moderate, a determination is made in step c5 as to whether or not the peak point heartbeat timer has begun counting up. In this case, since counting up of the peak point heartbeat timer has not begun, the processing proceeds to step c6, where counting up of the peak point heartbeat timer is begun, and a determination is made in step c7 as to whether or not the absolute value of a gradient $D_{RH}$ of the present peak point heartbeat rate $R_{HP(n)}$ and the previous peak point heartbeat rate $R_{HP_{n-1}}$ is less than 1. Also, when it is determined in step c5 that the peak point heartbeat timer has begun counting up, the processing proceeds to step c7.

When it is determined in step c7 that the absolute value of gradient $D_{RH}$ of the adjacent peak point heartbeat rate $R_{HP}$ is less than 1, that is, the peak point heartbeat rate $R_{HP}$ is increasing or decreasing slightly, the processing proceeds to step c8, where a determination is made as to whether or not a peak point heartbeat gradient timer has begun counting up. In this case, the peak point heartbeat gradient timer does not begin counting up and the processing proceeds to step c9, where the peak point heartbeat timer begins to count up, and a determination is made in step c10 as to whether or not the count value $T_{CP}$ of the peak point heartbeat timer is a predetermined time $T_{RP}$, for example, 30 seconds, or more. Also, when it is determined in step c8 that the peak point heartbeat gradient timer has begun counting up, the processing proceeds to step c10.

When it is determined in step c10 that the count value $T_{CP}$ of the peak point heartbeat timer is the preset time $T_{RP}$ or more, that is, a condition where the variation width of peak point heartbeat rate has continued for a long time, a determination is made in step c11 as to whether or not the count value $T_{CD}$ of the peak point heartbeat gradient timer is the preset time $T_{RD}$, for example, 30 seconds, or more.

When it is determined in step c11 that the count value $T_{CD}$ of the peak point heartbeat gradient timer is more than the preset time $T_{RD}$, that is, a condition where the peak point heartbeat rate increasing or decreasing slightly has continued for a long time, a stable awareness condition experienced flag $F_{WS}$ is set in step c12, the 30-sec average heartbeat rate $R_{A30(n)}$ is adopted as a reference heartbeat rate $R_{HB}$, the count value $T_{CP}$ of the peak point heartbeat timer and the count value $T_{CD}$ of the peak point heartbeat gradient timer are individually reset to 0 in step c14, and the processing returns to step c1 according to the next interrupt signal.

Further, when it is determined in step c3 that the absolute value of the 30-sec average heartbeat rate $R_{A30(n)}$ subtracted by the 10-point running average heartbeat rate $R_{A10(n)}$ exceeds 2, that is, the change in heartbeat rate of the driver is relatively large, or when it is determined in step c1 that absolute value of the present peak point heartbeat rate $R_{HP(n)}$ subtracted by the previous peak point heartbeat rate $R_{HP(n-1)}$ is 2 or more, that is, the peak point heartbeat rate $R_{HP}$ increases or decreases relatively sharply, or when it is determined in step c7 that the absolute value of gradient $D_{RH}$ of the peak point heartbeat rate $R_{HP}$ is 1 or more, that is, the peak point heartbeat rate $R_{HP}$ increases or decreases relatively sharply, or when it is determined in step c10 that the count value $T_{CP}$ of the peak point heartbeat timer does not reach the preset time $T_{RP}$, that is, a small variation in the peak point heartbeat rate does not continue for a long time, or when it is determined in step c11 that the count value $T_{CD}$ of the peak point heartbeat gradient timer does not reach the preset time $T_{RD}$, that is, a condition where the peak point heartbeat rate increases or decreases very slightly does not continue for a long time, the processing proceeds to step c15, where a determination is made as to whether or not there was a peak point heartbeat rate $R_{HP}$ not smaller than the value of the reference heartbeat rate $R_{HB}$ subtracted by 3 and greater than the reference heartbeat rate $R_{HB}$ subtracted by 2 in the past 20 seconds.

When it is determined in step c15 that there was a peak point heartbeat rate $R_{HP}$ not smaller than the value of the reference heartbeat rate $R_{HB}$ subtracted by 3 and greater than the reference heartbeat rate $R_{HB}$ subtracted by 2 in the past 20 seconds, that is the driver has entered the transition area, the processing proceeds to step c16, where a transition condition flag $F_{ST}$ is set, and a determination is made in step c17 as to whether or not the stable awareness condition flag $F_{WS}$ is set. When it is determined in step c15 that there was not a peak point heartbeat rate $R_{HP}$ not smaller than the value of the reference heartbeat rate $R_{HB}$ subtracted by 3 and greater than the reference heartbeat rate $R_{HB}$ subtracted by 2 in the past 20 seconds, that is, the driver has not entered the transition area, the processing proceeds to step c17, and when it is determined in step c17 that the stable awareness condition flag $F_{WS}$ is not set, the processing returns to step c1 according to the next interrupt signal.

On the other hand, when it is determined in step c1 that the transition condition flag $F_{ST}$ is set, or when it is determined in step c17 that the stable awareness condition flag $F_{WS}$ is set, a determination is made in step c18 as to whether or not a warning preparation flag $F_{PR}$ described later is set. Since the warning preparation flag $F_{PR}$ is not set at the beginning, the processing proceeds to step c19, where a determination is made as to whether or not the value of the reference heartbeat rate $R_{HB}$ subtracted by the present 4-point running average heartbeat rate $R_{A4(n)}$ exceeds 0 and is less than or equal to 5. When it is determined in step c19 that the value of the reference heartbeat rate $R_{HB}$ subtracted by the present 4-point running average heartbeat rate $R_{A4(n)}$ exceeds 0 and less than or equal to 5, that is, the awareness of the driver tends to decrease, the warning preparation flag $F_{PR}$ is set in step c20, and the step of c1 and after is repeated according to the next interrupt signal.

When it is determined in step c18 that the warning preparation flag $F_{PR}$ is set, that is, the awareness of the driver tends to decrease, the processing proceeds to step c21, where a determination is made as to whether or not the value of the reference heartbeat rate $R_{HB}$ subtracted by the present heartbeat rate $R_{H(n)}$ is less than 5. When it is determined in step c21 that the value of the reference heartbeat rate $R_{HB}$ subtracted by the present heartbeat rate $R_{H(n)}$ is less than 5, that is, the decrease in heartbeat rate is relatively small, the processing proceeds to step c22, where the warning level $L_W$ is set to the first level, and the processing returns to step c1 according to the next interrupt signal. When it is determined in step c21 that the value of the reference heartbeat rate $R_{HB}$ subtracted by the present heartbeat rate $R_{H(n)}$ is 5 or more, that is, the decrease in heartbeat rate is relatively large, the processing proceeds to step c19. When it is determined in step c19 that the value of the reference heartbeat rate $R_{HB}$ subtracted by the present 4-point running average heartbeat rate $R_{A4(n)}$ is greater than 5, that is, the decrease in heartbeat rate of the driver is very large, the processing proceeds to step c23, where a determination is made as to whether or not the absolute value of the present peak point heartbeat rate $R_{HP(n)}$ subtracted by the previous peak point heartbeat rate $R_{HP(n-1)}$ is greater than 4.

When it is determined in step c23 that the absolute value of the present peak point heartbeat rate $R_{HP(n)}$ subtracted by the previous peak point heartbeat rate $R_{HP(n-1)}$ is greater than 4, that is, the driver is quickly becoming less aware, the processing proceeds to step c24, where a determination is made as to whether or not the adjacent peak point heartbeat timer has begun counting up. When it is determined that the adjacent peak point heartbeat timer has not begun counting up, the adjacent peak point heartbeat timer begins counting up in step c25, the adjacent peak point data number $N_{DB}$ is increased by 1 in step c26, and a determination is made in step c27 as to whether or not the count value $T_{CB}$ of the adjacent peak point heartbeat timer exceeds a preset time $T_{RB}$, for example, 20 seconds. When it is determined in step c24 that the adjacent peak point heartbeat timer has begun counting up, the processing proceeds to step c26.

When it is determined in step c27 that the count value $T_{CB}$ of the adjacent peak point heartbeat timer exceeds the preset time $T_{RB}$, that is, the driver's heartbeat rate varies to a large extent, the processing proceeds to step c28, where the count value $T_{CB}$ of the adjacent peak point heartbeat timer is reset to 0, the adjacent peak point heartbeat data number $N_{DB}$ is also rest to 0 in step 29, the warning level is set to the second level in step c30, and the processing returns to step c1 according to the next interrupt signal. When it is determined in step c23 that the absolute value of the present peak point heartbeat rate $R_{HP(n)}$ subtracted by the previous peak point heartbeat rate $R_{HP(n-1)}$ is 4 or less, that is, the driver's awareness continues to decrease, the processing proceeds to step c30, where the warning level is set to the second level.

Further, when it is determined in step c27 that the count value $T_{CB}$ of the adjacent peak point heartbeat timer is the preset time $T_{RB}$ or less, that is, large variations in the driver's heartbeat rate do not continue for a long time, the processing proceeds to step c31, where a determination is made as to whether or not the adjacent peak point heartbeat data number $N_{DB}$ is more than 3. When it is determined that the adjacent peak point heartbeat data number $N_{DB}$ is more than 3, that is, the driver's awareness periodically decreases, the processing proceeds to step c32, where the warning level is set to the third level, and the processing returns to step c1 according to the next interrupt signal. When it is determined in step c31 that the adjacent peak point heartbeat data number $N_{DB}$ is less than 3, that is, the driver's awareness is not periodically decreasing, the processing proceeds to step c30.

In order to drive the vehicle exactly according to the road shape, the driver coarsely steers the steering wheel 33 according to curves in the road, and more finely steers the vehicle according to the road condition. That is, to drive on the road from the present position of the driver to a target position, the steering wheel 33 is coarsely controlled according to the road shape and, when the driver controls the vehicle according to the road condition, the steering wheel 33 is finely steered according to the position of the vehicle relative to the road every moment. The fine steering of the steering wheel 33 can be detected to determine the awareness of the driver.

Figure 23:
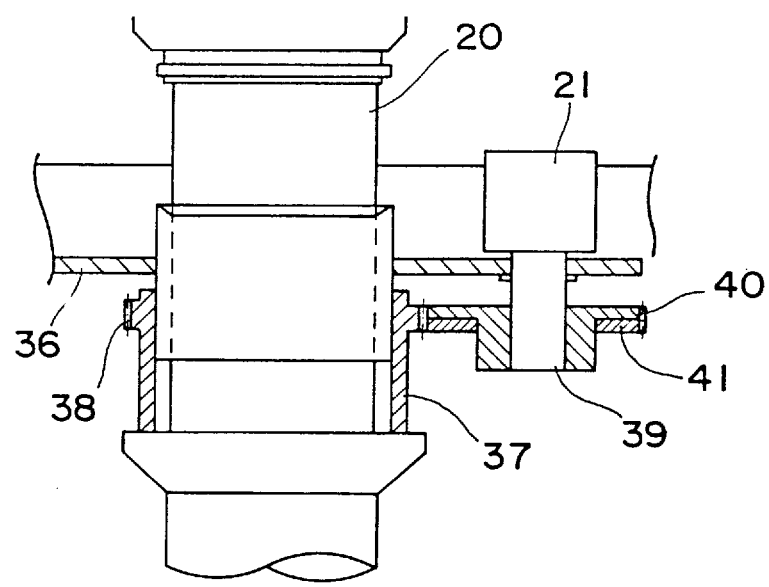
FIG. 23 is a schematic enlarged view showing part of the steering shaft to which the steering angle sensor is mounted.

FIG. 23 illustrates an enlarged cross-sectional structure of the steering shaft 20 to which the steering angle sensor 21 is mounted. The steering shaft 20, provided integrally with the steering wheel 33, is rotatably mounted on a steering column 36, the steering shaft 20 is provided with a gear cylinder 37 integrally and coaxially, and the gear cylinder 37 is integrally formed with a drive gear 38. The steering column 36 is provided adjacent to the steering shaft 20 with the steering angle sensor 21, which is a potentiometer, a rotary shaft 39 of the steering angle sensor 21 is provided integrally with a drive gear 40 and engaged with a backlash removing gear 41 which is rotatable relative to the drive gear 40. The drive gear 38 of the gear cylinder 37 engages with the drive gear 40 and the backlash removing gear 41.

Therefore, when the steering wheel 33 is operated, the steering shaft 20 rotates accordingly, and the drive gear 40 is rotated by the backlash removing gear 41 of which the phase relative to the drive gear 40 is previously adjusted. Rotation exactly corresponding to the turning of the steering shaft 20 is transmitted to the rotary shaft 39 of the steering angle sensor 21. A turning condition of the steering shaft 20 is exactly detected by the steering angle sensor, which is output as an electrical signal.

The vehicle speed sensor 24 detects rotation of the output shaft of the transmission (not shown in the present embodiment), however, it is possible to employ other known types of vehicle sensors which detect the vehicle speed according to the rotation speed of the driven wheels.

The steering angle data processing means 22 calculates a standard value of the steering component which is frequency analyzed to determine the awareness of the driver according to detection signals from the steering angle sensor 21 and the vehicle speed sensor 24, and processes the absolute value of the detection signal of the steering angle sensor 21, which is bandpass filtered using a running average equation to obtain steering angle data. Specifically, the steering angle data is sequentially received every 0.1 see with a sampling frequency of 10 Hz. The steering angle data is FFT (Fast Fourier Transform) analyzed to obtain magnitudes (power spectrum) of components of individual frequency bands.

Figure 24:
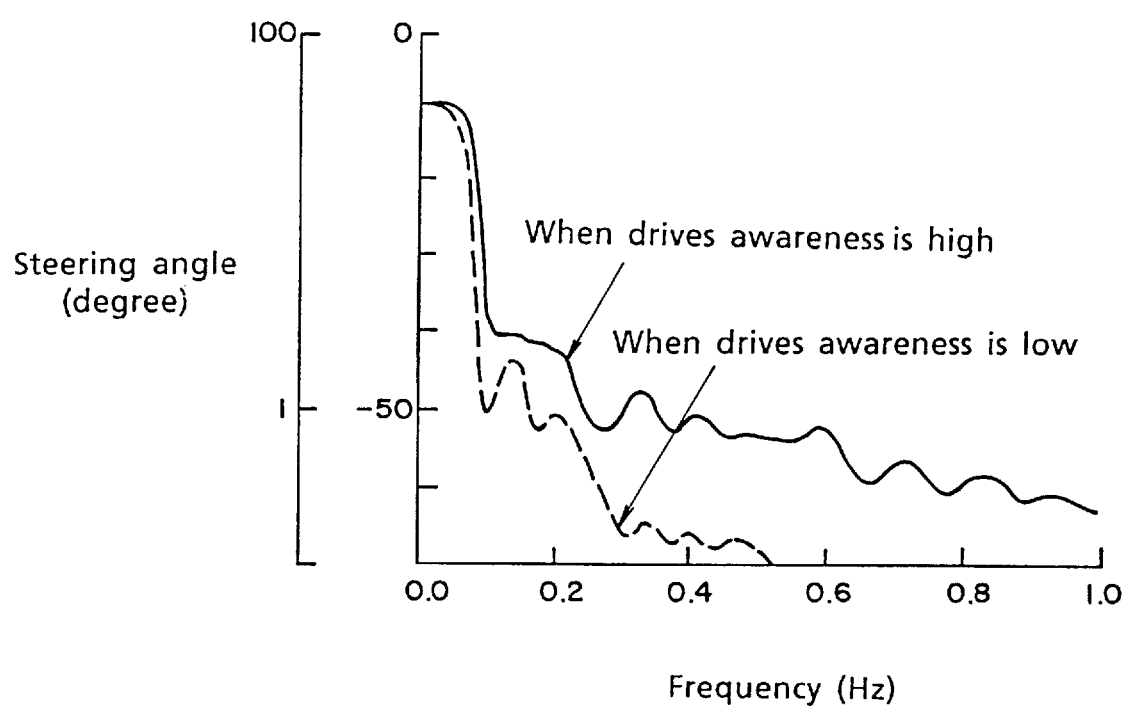
FIG. 24 is a graph showing a visual steering component of the driver versus steering angle frequency distribution of the steering wheel.

FIG. 24 is a graph showing the obtained frequency distribution of steering angle signal of the steering wheel 33 vs, motion characteristics of the driver, in which the solid lines indicate an ordinary driver with high awareness, and the broken lines indicate the driver with decreased awareness. In the graph, 1 Hz means 1 turn per second of the steering wheel 33, 0.1 Hz means 1 turn per 10 seconds of the steering wheel 33, and 0.5 Hz means 1 turn per 2 seconds of the steering wheel 33. As can be seen from the graph, the frequency of fine manipulation of the steering wheel 33 increases with increasing driver awareness, and the frequency of fine manipulation of the steering wheel 33 decreases with decreasing driver awareness. Therefore, it is possible to determine the awareness of the driver by detecting only the area of fine manipulation of the steering wheel 33 and comparing it with a preset reference value.

That is, detection data is divided into predetermined frequency bands by determining an average value of a plurality of points of every sampling period from the present to the past by a low-pass filter of less than a predetermined frequency, that is, by running average calculation. Specifically, from the graph shown in FIG. 24, the 0.3–1.0 Hz component of fine manipulation of the steering wheel 33 is set as an area of visual steering component (hereinafter referred to as "visual steering component"), a component of less than 0.3 Hz is cut off because this area represents coarse manipulation of the steering wheel 33 according to curves in the road, and a component of more than 1.0 Hz is also cut off.

The above visual steering component will be described later in detail.

Division into frequency bands is achieved by a running average calculation. In general, where a sampling interval is Is, and a cut-off frequency is f, the number M of the samples to be averaged can be determined by the equation shown below:

$$M = 0.443/(Is \cdot f).$$

Therefore, to determine a steering component area $S_H$ of less than 1.0 Hz, a number $M_H$ of samples when the cut-off frequency of 1.0 Hz is calculated.

$$M_H = 0.443/(0.1 \times 1.0).$$

Further, to determine a steering component area $S_L$ of greater than 0.3 Hz, a number $M_L$ of samples when the cut-off frequency of 0.3 Hz is calculated.

$$M_L = 0.443/(0.1 \times 0.3).$$

Thus, the numbers for dividing the visual steering area S are calculated as $M_H=4$ and $M_L=15$.

Therefore, a 4-point running average steering angle $P_{A4}$ and a 15-point running average steering angle $P_{A15}$ of every sampling period from the present and past are calculated and, since the 1 second and 7 seconds, that is, the sampling periods are 0.1 second, a 10-point running average of the 4-point running average visual steering angle $P_{A4}$ (hereinafter referred to as "10×4 point running average steering angle") $P_{A4\text{-}10}$, a 70-point running average (hereinafter referred to as "70×4 point running average steering angle") $P_{A4\text{-}70}$, a 10-point running average of the 15-point running average steering angle (hereinafter referred to as "10×15 point running average steering angle) $P_{A15\text{-}10}$, and a 70-point running average (hereinafter referred to as "70×15 point running average steering angle) $P_{A15\text{-}70}$ are calculated. By determining the differences of these values, parameters $P_{S10}$ and $P_{S70}$ in the visual steering component area S can be calculated.

In the present embodiment, when preparing the graph showing the visual steering component of the driver vs. the frequency distribution of steering angle signal of the steering wheel 33 shown in FIG. 24, a predetermined traveling test is carried out to determine the visual steering component of an aware driver during ordinary traveling (solid lines) and the visual steering component of an unaware (asleep) driver (broken lines).

In general, a driver manipulates the steering wheel 33 to trace the traveling lane of the road or his target course in view of the traveling speed based on visual information of "road shape in front of the vehicle" and "present position of the vehicle on the road". The present inventors discovered that when part of the visual information is limited, the limitation of visual information affects the operation characteristics of the steering wheel 33. That is, visual steering is controlled mainly by limitation of the driver's visual information, traveling speed, and individual differences on the steering angle frequency response of the steering wheel 33. This was announced at the "Dynamic and Design Conference 1992" of the Society of Mechanical Engineering on Jul. 7–8, 1992, of which test results are briefly described below.

Figure 26:
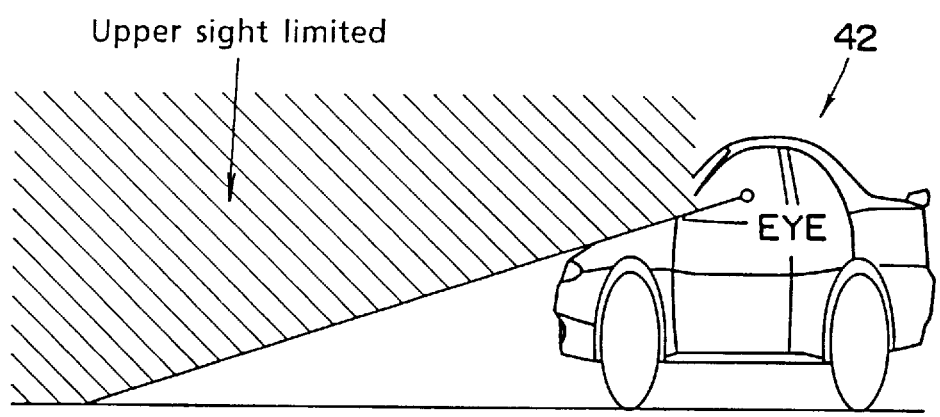
FIG. 26 is a schematic view illustrating an upward sight limitation is on the driver.

In tests conducted to determine the operation characteristics of the steering wheel 33 by the driver, using a predetermined curved road, the vehicle traveled at a predetermined speed with part of the driver's masked. Specifically, as shown in FIG. 26, a traveling test was carried out with the driver's forward sight at a predetermined distance of a vehicle 42, and steering angle data of the steering wheel 33 was frequency analyzed to determine the operation characteristics. As a result, when ordinary traveling and traveling with limited upward sight were frequency analyzed, a conspicuous difference was noted between both cases in the range from 0.3 to 1.0 Hz. It can be estimated from the result that the data of the 0.3–1.0 Hz area proves accurate feedback correction steering control of the positional relation between the vehicle 42 and the road in front of the vehicle 42.

Since the driver's upward sight was limited in this test, the visual steering component was more apparent than during ordinary traveling.

Figure 25:
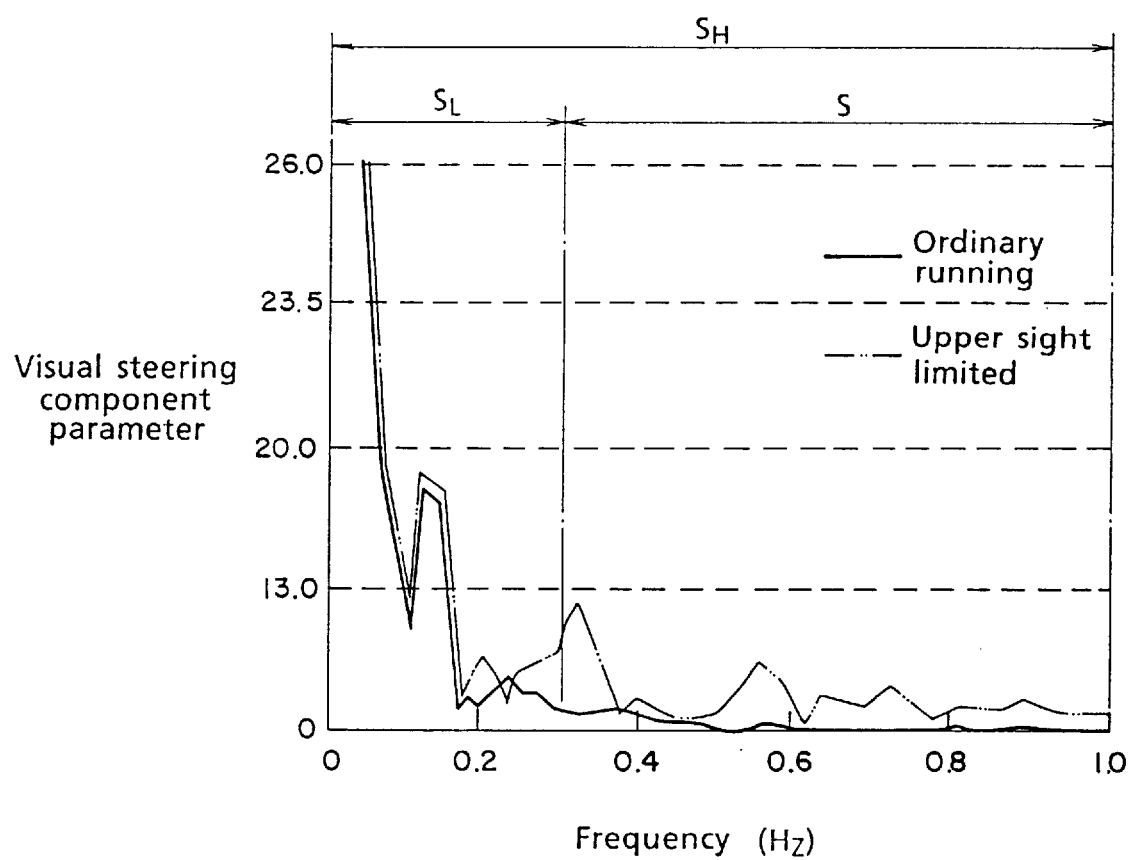
FIG. 25 is a graph showing a steering angle frequency distribution of the steering wheel when an upward sight limitation is placed on the driver.

Therefore, the fine steering component of the steering wheel 33, that is, the visual steering component can be detected by frequency analyzing steering angle data of the steering wheel 33, and extracting data of the 0.3–1.0 Hz area. Further, as can be seen from the fact that the result agrees with the tendency of the graph shown in FIG. 25, the level of awareness of the driver can be determined from data of the visual steering component area.

Figure 27:
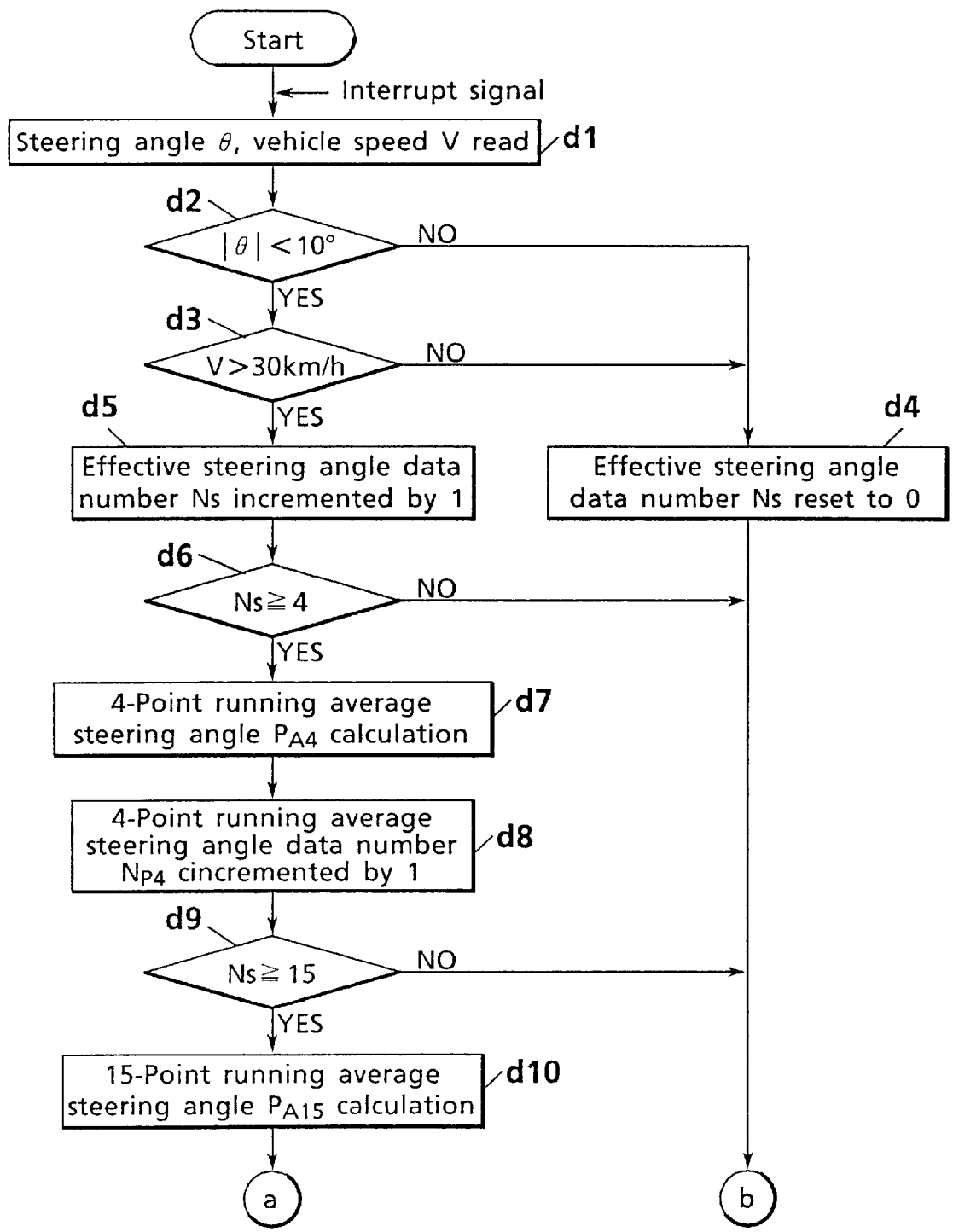
FIG. 27 is a flow chart showing processing performed by the steering angle data processing means of the present embodiment along with FIG. 28.
Figure 28:
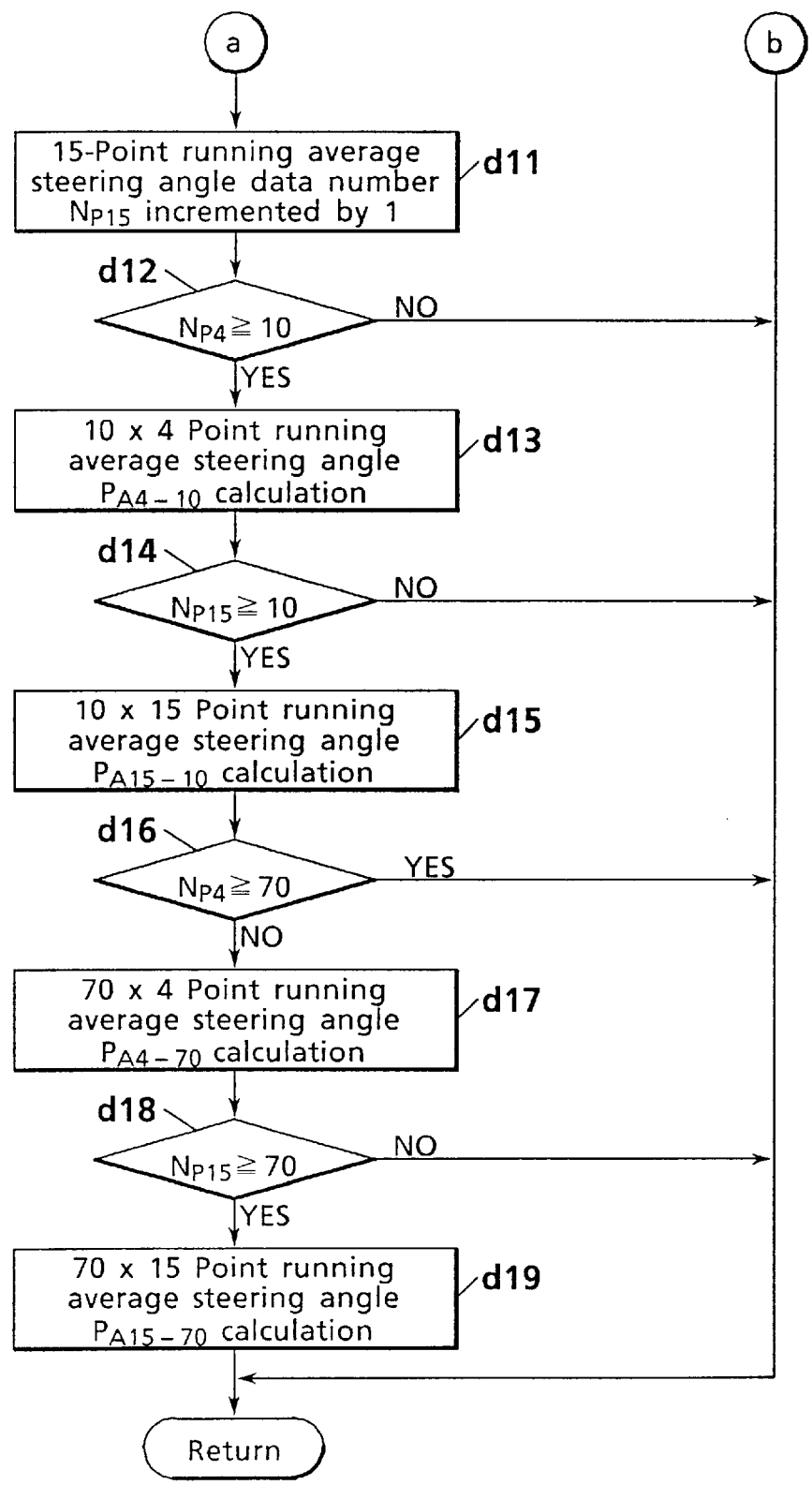
FIG. 28 is a flow chart showing processing performed by the steering angle data processing means of the present embodiment along with FIG. 27.

Processing flow in the steering angle data processing means 22 in the present embodiment is shown in FIG. 27 and FIG. 28. Specifically, processing by the steering angle data processing means 22 in the present embodiment is performed in a predetermined period, that is, upon receipt of an interrupt signal of every 15 msec. First, in step d1, a steering angle θ from the steering angle sensor 21 and a vehicle speed V from the vehicle speed sensor 24 are read at every sample period of 0.1 second. A determination is made in step d2 as to whether or not the absolute value of the read steering angle θ is less than 10°, when it is determined that the absolute value of the steering angle θ is less than 10°, the processing proceeds to step d3. When the absolute value of the steering angle θ is determined to be 10° or more, the processing proceeds to step d4, where the past effective steering angle data number $N_S$ is reset, and the processing returns to step d1. When the vehicle is traveling with a steering angle θ of 10° or more, this is a time when the driver coarsely controls the steering wheel 33, which is not proper as data for determining the visual steering component required for determining the awareness of the driver.

A determination is made in step d3 as to whether or not the read vehicle speed V is 30 km/h or more, and when it is determined that the vehicle speed V is 30 km/h or more, the processing proceeds to step d5. When it is determined that the vehicle speed V is less than 30 km/h, the processing proceeds to step d4, where, as described above, the steering angle data number $N_S$ is reset to 0, and the processing returns again to step d1. The case when the vehicle speed V is less than 30 km/h, for example, when the vehicle travels at a low speed on a crowded road is also considered. In such a case, since the driver may perform meaningless manipulations of the steering wheel 33, data which is inappropriate for determining the awareness of the driver may be input. Therefore, as described above, when the absolute value of the steering angle θ is 10° or more or the vehicle speed V is less than 30 km/h, the read steering angle θ is not adopted in step d4.

In step d5, the effective steering angle data number $N_S$ adopted in steps d2 and d3 is incremented by 1. A determination is made in step d6 as to whether or not the effective steering angle data number $N_S$ is 4 or more, and when it is determined to be 4 or more, the processing proceeds to step d7. The 4-point running average steering angle $P_{A4}$ is calculated in step d7, and the processing proceeds to step d8, where the 4-point running average steering angle data number $N_{P4}$ of the 4-point running average steering angle $P_{A4}$ calculated in step d7 is incremented by 1. When it is determined in step d6 that the effective steering angle data number $N_S$ is not 4 or more, since the 4-point running average steering angle $P_{A4}$ cannot be calculated in step d7, the processing returns to step d1.

In step d9, a determination is made as to whether or not the effective steering angle data number $N_S$ is 15 or more, and when it is determined to be 15 or more, the processing proceeds to step d10. In step d10, the 15-point running average steering angle $P_{A15}$ is calculated, and the processing proceeds to step d11, where the 15-point running average steering angle $P_{A15}$ is incremented by 1. When it is determined in step d9 that the 15-point running average steering angle data number $N_S$ is not 15 or more, since the 15-point running average steering angle $P_{A15}$ cannot be calculated in step d10, the processing returns to step d1.

In step d12, a determination is made as to whether or not the 4-point running average steering angle data number $N_{P4}$ is 10 or more, and when it is determined to be 10 or more, the processing proceeds to step d13, where the above-described 10×4 point running average steering angle $P_{A4-10}$ is calculated, and the processing proceeds to step d14. A determination is made in step d14 as to whether or not the 15-point running average steering angle data number $N_{P15}$ is 10 or more, and when it is 10 or more, the processing proceeds to step d15, where the above-described 10×15 point running average steering angle $P_{A15-10}$ is calculated, and the processing proceeds to d16. When it is determined in steps d12 and d14 that the 4-point running average steering angle data number $N_{P4}$ or the 15-point running average steering angle data number $N_{P15}$ is not 10 or more, since the 10×4 point running average steering angle $P_{A4-10}$ and the 10×15 point running average steering angle $P_{A15-10}$ cannot be calculated in steps d13 and d15, the processing returns to step d1.

In step d16, a determination is made as to whether or not the 4-point running average steering angle data number $N_{P4}$ is 70 or more, and when it is determined to be 70 or more, the processing proceeds to step d17, where the above-described 70×4 point running average steering angle $P_{A4-70}$ is calculated, and the processing proceeds to step d18. A determination is made in step d18 as to whether or not the 15-point running average steering angle data number $N_{P15}$ is 70 or more, and when it is 70 or more, the processing proceeds to step d19, where the above-described 70×15 point running average steering angle $P_{A15-70}$ is calculated. When it is determined in steps d16 and d18 that the 4-point running average steering angle data number $N_{P4}$ or the 15-point running average steering angle data number $N_{P15}$ is not 70 or more, since the 70×4 point running average steering angle $P_{A4-70}$ and the 70×15 point running average steering angle $P_{A15-70}$ cannot be calculated in steps d17 and d19, the processing returns to step d1.

The steering awareness determination means 23 determines the present awareness of the driver according to the reference value (hereinafter referred to as "reference parameter") of a steering component frequency analyzed to reflect the awareness of the driver calculated by the steering angle data processing means 22, and sets the warning level corresponding to the awareness level. That is, from the 10×4 point average steering angle $P_{P4-10}$ and the 70×4 point running average steering angle $P_{A4-70}$, and the 10×15 point running average steering angle $P_{A15-10}$ and the 70×15 point running average steering angle $P_{A15-70}$, parameters $P_{S10}$ and $P_{S70}$ of the visual steering component area S are calculated by the following equations:

$$P_{S10}=|P_{A4-10}-P_{A15-10}|,$$

$$P_{S70}=|P_{A4-70}-P_{A15-70}|.$$

Then, the parameters $P_{S10}$ and $P_{S70}$ of the visual steering component area S are compared with preset reference parameters to determine the level of awareness of the driver.

Figure 29:
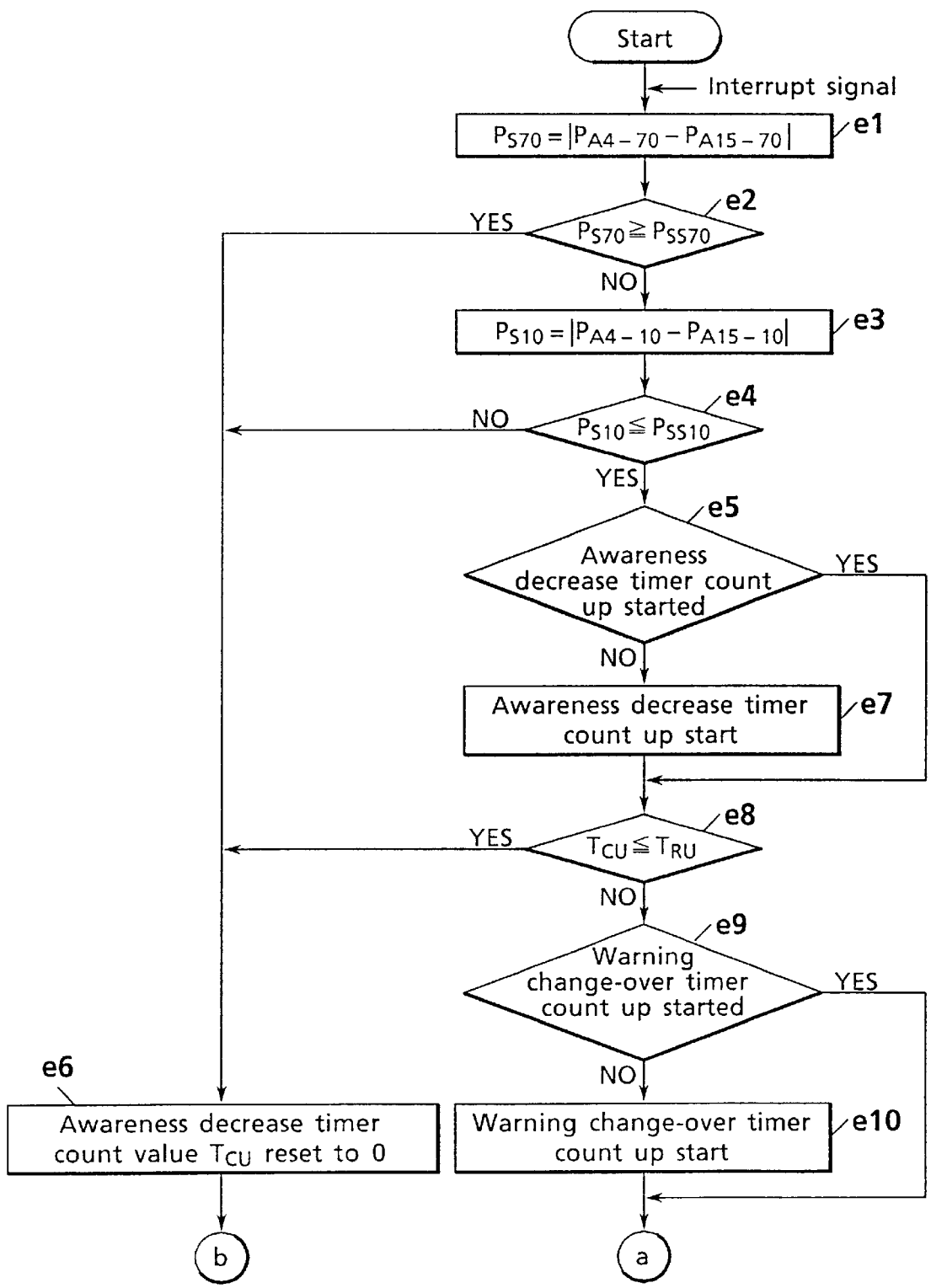
FIG. 29 is a flow chart showing processing performed by the steering awareness determination means of the present embodiment along with FIG. 30.
Figure 30:
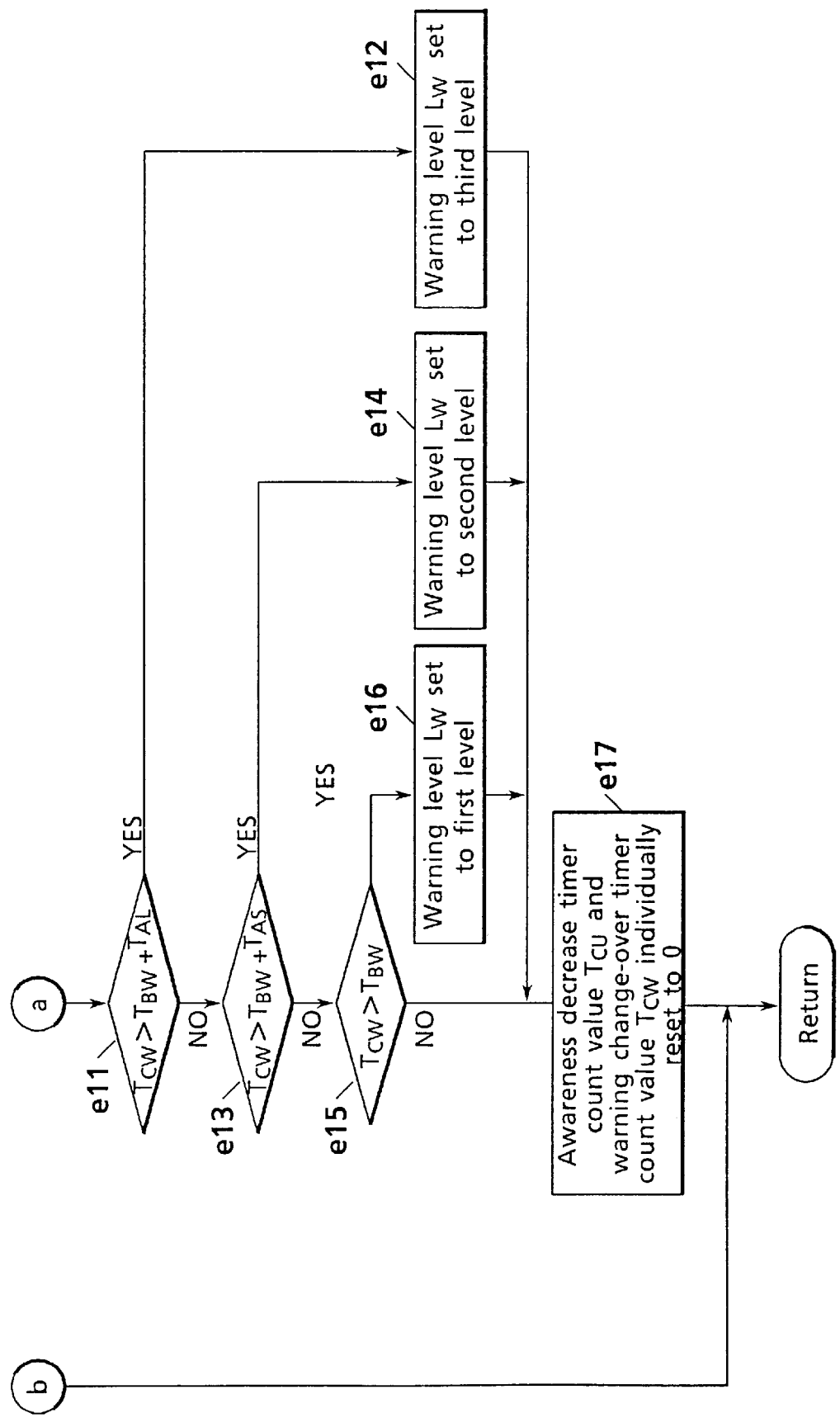
FIG. 30 is a flow chart showing processing performed by the steering awareness determination means of the present embodiment along with FIG. 29.

The processing flow in the steering awareness determination means 23 in the present embodiment is shown in FIG. 29 and FIG. 30. Specifically, processing in the steering awareness determination means 23 in the present embodiment is carried out at every interrupt signal, for example, of 15 msec. First, in step e1, the parameter $P_{S70}$ of the visual steering component area S is calculated from the absolute value of difference between the 70×4 point running average steering angle $P_{A4-70}$ and the 70×15 point running average steering angle $P_{A10-70}$. A determination is made in step e2 as to whether or not the calculated parameter $P_{S70}$ of the visual steering component area S is not less than the reference parameter $P_{SS70}$, and when the parameter $P_{S70}$ of the visual steering component area S is less than the reference parameter $P_{SS70}$, the processing proceeds to step e3.

In step e3, the parameter $P_{S10}$ of the visual steering component area S is calculated from the absolute value of difference between the 10×4 point running average steering angle $P_{A4-10}$ and the 10×15 point running average steering angle $P_{A10-10}$. A determination is made in step e4 as to whether or not the parameter $P_{S10}$ of the visual steering component area S is not more than the reference parameter $P_{SS10}$, and when the parameter $P_{S10}$ of the visual steering component area S is not more than the reference parameter $P_{SS10}$, the processing proceeds to step e5.

The reference parameter is set according to the level of awareness of the driver and, in the present embodiment, 0.21 is set as the reference parameter $P_{SS70}$ corresponding to the visual steering component parameter $P_{S70}$ and 0.17 is set as the reference parameter $P_{SS10}$ corresponding to the visual steering component parameter $P_{S10}$. The calculated parameters $P_{S10}$ and $P_{S70}$ of the visual steering component area S are compared with the reference parameters $P_{SS70}$ and $P_{SS10}$ to set the warning level $L_W$. The reference parameters $P_{SS70}$ and $P_{SS10}$, as described above, are set according to the graph shown in FIG. 24 showing the visual steering components of traveling where the awareness of the driver is low and traveling where the awareness level of the driver is high relative to the frequency distribution. These values are not limited to those in the above embodiment, but may be appropriately set according to various conditions.

When it is determined that the parameter $P_{S70}$ of the visual steering component area S calculated in step e2 is greater than the reference parameter $P_{SS70}$, the processing proceeds to step e6. When it is determined that the parameter $P_{S10}$ of the visual steering component area S calculated in step e4 is greater than the reference parameter $P_{SS10}$, the processing proceeds to step e6. In step e6, since the level of awareness of the driver is determined to be high, the count value $T_{CU}$ of the awareness decrease timer is reset to 0, and step e1 is repeated according to the next interrupt signal.

In step e5, a determination is made as to whether or not the awareness decrease timer begins counting up and, when it is determined not to be counting up, counting up of the awareness decrease timer is begun in step e7, a determination is made in step e8 as to whether or not the count value $T_{CU}$ of the awareness decrease timer is not more than a preset time $T_{RU}$, for example, 3 seconds, that is, $P_{S70} \geq P_{SS70}$ and $P_{S10} \leq P_{SS10}$. When it is determined to be not more than the preset time $T_{RU}$, the processing proceeds to step e6, where the count value $T_{CU}$ of the awareness decrease timer is reset to 0, otherwise, the processing proceeds to step e9.

In step e9, a determination is made as to whether or not a warning change-over timer begins counting up and, when it is determined not to be counting up, counting up of the warning change-over timer begins in step e10, and a determination is made in step e11 as to whether or not the count value $T_{CW}$ of the warning change-over timer is longer than a preset reference warning change-over time $T_{BW}$ added with a preset first additional time $T_{AL}$, for example, 4 seconds. When it is determined that the count value $T_{CW}$ of the warning change-over timer is longer than the sum of the reference warning change-over time $T_{BW}$ and the first additional time $T_{AL}$, that is, the awareness level of the driver decreases to its lowest level, the processing proceeds to step e12, where the warning level $L_W$ is set to the third level, and the processing proceeds to step e17 which will be described later.

When it is determined in step e11 that the count value $T_{CW}$ of the warning change-over timer is not longer than the sum of the reference warning change-over time $T_{BW}$ and the first additional time $T_{AL}$, the processing proceeds to step e13, where a determination is made as to whether or not the count value $T_{CW}$ of the warning change-over timer is longer than the sum of the reference warning change-over time $T_{BW}$ and a preset second additional time $T_{AS}$, for example, 3 seconds. When it is determined that the count value $T_{CW}$ of the warning change-over timer is longer than the sum of the reference warning change-over time $T_{BW}$ and the second additional time $T_{AS}$, the processing proceeds to step e14, where the warning level $L_W$ is set to the second level.

When it is determined in step e13 that the count value $T_{CW}$ of the warning change-over timer is not longer than the sum of the reference warning change-over time $T_{BW}$ and the second additional time $T_{AS}$, the processing proceeds to step e15, where a determination is made as to whether or not the count value $T_{CW}$ of the warning change-over timer is longer than the reference warning change-over time $T_{BW}$. When it is determined that the count value $T_{CW}$ of the warning change-over timer is longer than the reference warning change-over time $T_{BW}$, the processing proceeds to step e16, where the warning level $L_W$ is set to the first level, and the processing proceeds to step e17 which will be described later.

When it is determined in step e15 that the count value $T_{CW}$ of the warning change-over timer is not more than the reference warning change-over time $T_{BW}$, the processing proceeds to step e17, where the count value $T_{CU}$ of the awareness decrease timer and the count value $T_{CW}$ of the warning change-over time are individually set to 0, and then the step of e1 is repeated according to the next interrupt signal.

In the tactile warning means 26, a pair of right and left side supports 44 provided in the seat back 43 of the driver's seat 25 are made rotatable in the direction of the arrow to repeatedly press the driver's side sitting on the seat 25 from both sides, or separate the side supports 44 from the driver's side, thereby improving the awareness of the driver by tactile excitation. The device is adapted to operate when the driver's grip of the steering wheel 33 is not correct, or according to the warning level $L_W$ of the first level.

Further, in the visual warning means 28, a display 45 for displaying a sleep drive warning is embedded in the front window 27 in front of the driver's seat 25 which is transparent and does not block the driver's sight when unenergized and, when energized, a sleep warning mark 46 as shown in FIG. 2, for example, is turned on and off in the transparent condition, thereby improving the awareness of the driver by visual excitation. The device is adapted to operate according to the warning level $L_W$ of the second level.

Further, the auditory warning means 29 sounds a warning buzzer 48 incorporated in an instrument panel 47 to improve the awareness of the driver by auditory excitation. The device is adapted to operate when the driver's grip of the steering wheel 33 is not correct, or according to the warning level $L_W$ of the third level.

The steering wheel grip defect warning means 34 in the present embodiment, as described above, operates in conjunction with the two warning means 26 and 29. By changing the movement of the side supports 44 and the sound of the warning buzzer 48, the driver can easily distinguish between when the steering wheel 33 is gripped incorrectly and when the awareness level of the driver is decreasing.

The warning control means 30 controls operation of the three warning means 26, 28, and 29 according to the warning levels $L_W$ individually determined by the heartbeat awareness determination means 19 and the steering awareness determination means 23. When an ON operation signal of the warning release switch 31 is input by the driver, the operation of the three warning means 26, 28, and 29 according to the warning level $L_W$ is stopped. However, when the warning means 26 and 29 are operated as the steering wheel grip defect warning means 34, the operation of these devices is not stopped even if the driver turns on the warning release switch 31.

Figure 31:
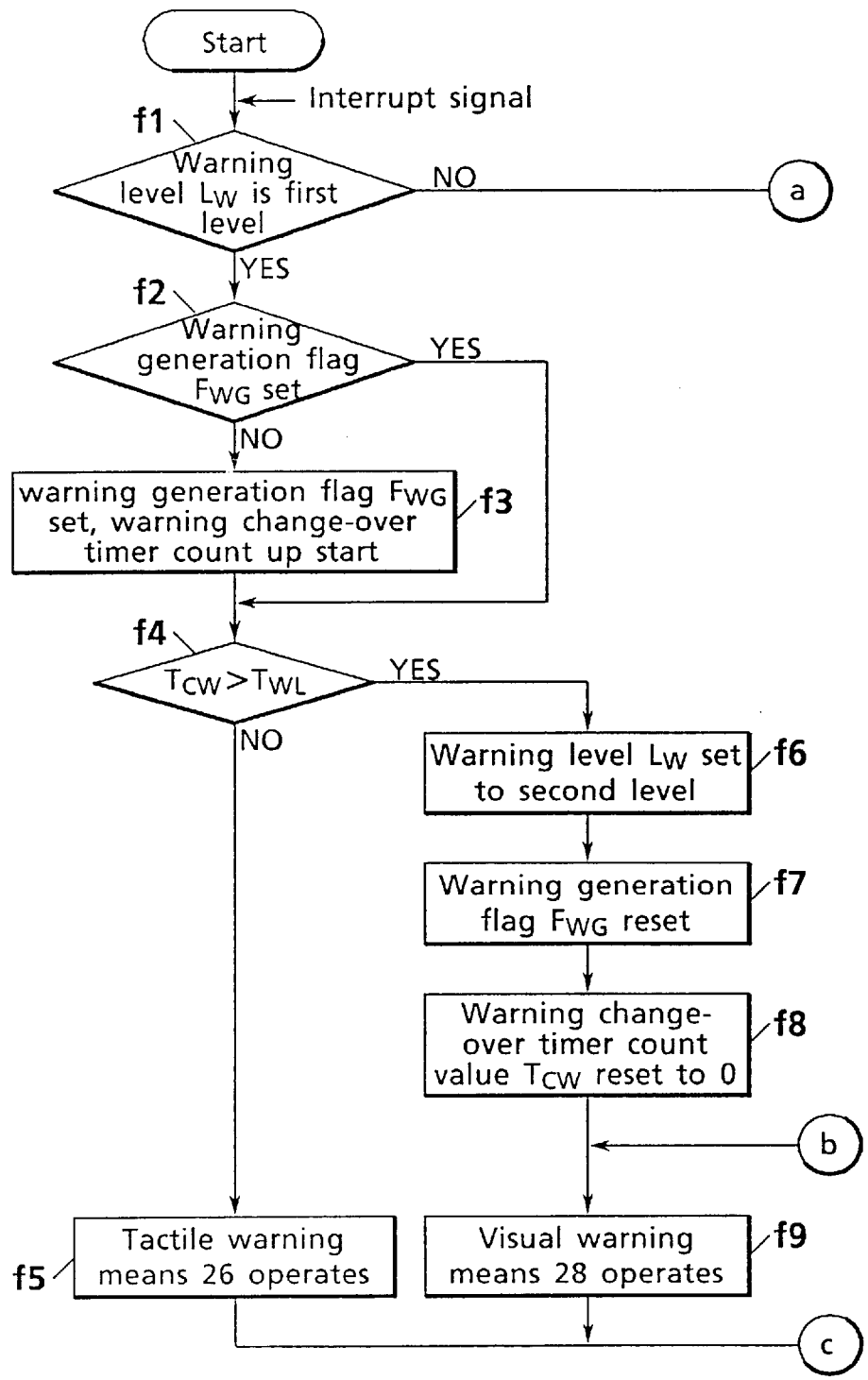
FIG. 31 is a flow chart showing warning processing performed by the warning control means of the present embodiment along with FIG. 32.
Figure 32:
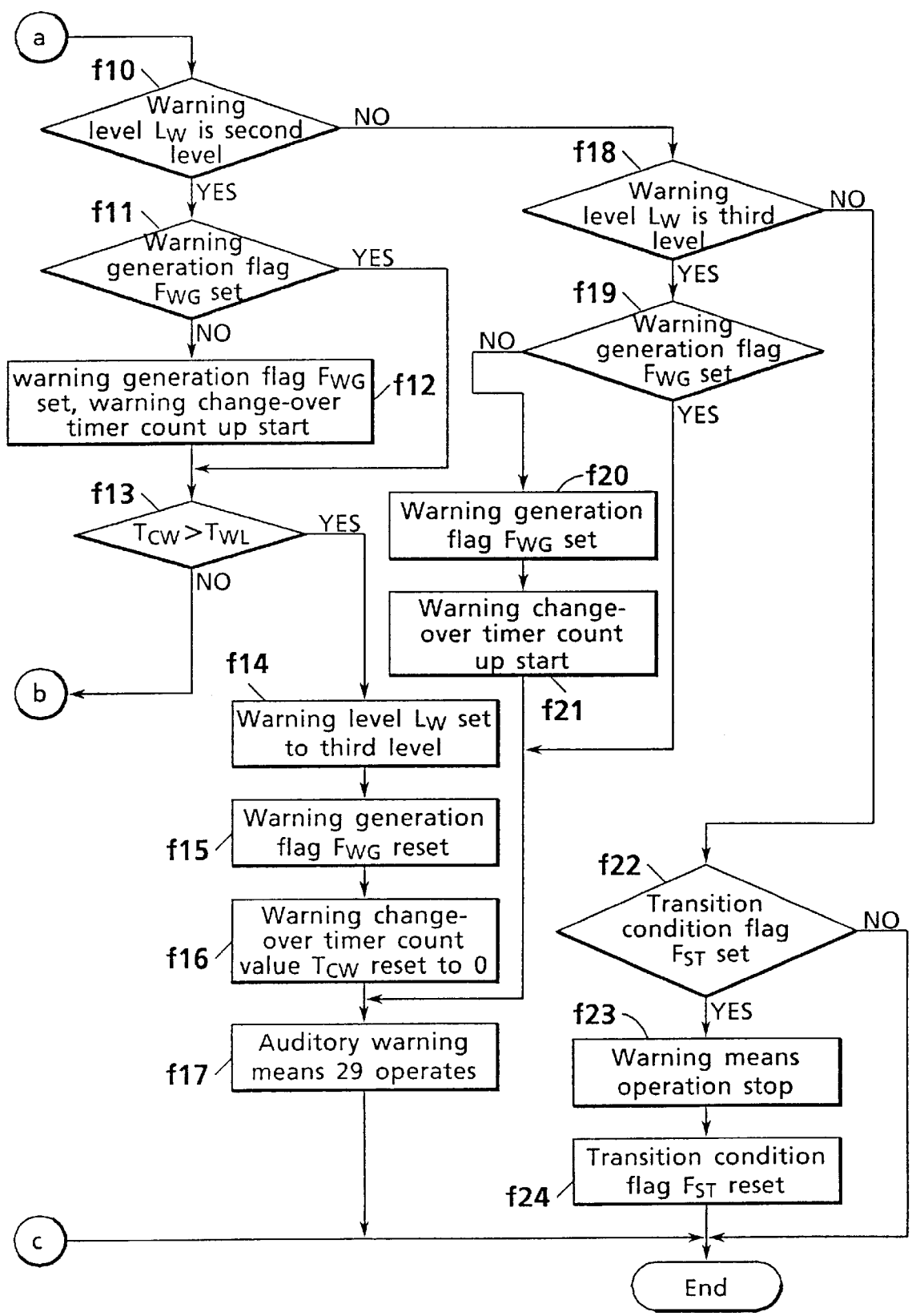
FIG. 32 is a flow chart showing warning processing performed by the warning control means of the present embodiment along with FIG. 31.

A warning processing flow of the warning control means 30 is shown in FIG. 31 and FIG. 32. Specifically, warning processing in the present embodiment is carried out for every interrupt signal of 15 msec, for example. First, a determination is made in step f1 as to whether or not the warning level $L_W$ is the first level, and when the warning level $L_W$ is the first level, the processing proceeds to step f2, where a determination is made as to whether or not a warning generation flag $F_{WG}$ is set. When it is determined in step f2 that the warning generation flag $F_{WG}$ is not set, the warning generation flag $F_{WG}$ is set in step f3, and counting up of the warning change-over timer begins, and a determination is made in step f4 as to whether or not the count value $T_{CW}$ of the warning change-over timer exceeds the first preset time $T_{WL}$, for example, 10 seconds.

When it is determined in step f4 that the count value $T_{CW}$ of the warning change-over timer is not more than the first preset time $T_{WL}$, the processing proceeds to step f5, where the tactile warning means 26 is operated to press or separate the side supports 44 relative to the side of the driver, thereby improving the awareness of the driver by tactile excitation, and the processing returns to step f1 according to the next interrupt signal.

When it is determined in step f2 that the warning generation flag $F_{WG}$ is set, the processing proceeds to step f4, where a determination is made again as to whether or not the count value $T_{CW}$ of the warning change-over timer exceeds the first preset time $T_{WL}$.

When it is determined in step f4 that the count value $T_{CW}$ of the warning change-over timer exceeds the first preset time $T_{WL}$, that is, the awareness of the driver is not improved by only the operation of the tactile warning means 26, the processing proceeds to step f6, where the warning level $L_W$ is set to the second level, the warning generation flag $F_{WG}$ is reset to 0 in step f7, the count value $T_{CW}$ of the warning change-over timer is reset to 0 in step f8, the visual warning means 28 is operated in step f9 to display the warning mark 46 on the front window 27 to improve the awareness of the driver by visual excitation, and the processing returns to step f1 according to the next interrupt signal.

When it is determined in step f1 that the warning level $L_W$ is not the first level, the processing proceeds to step f10, where a determination is made as to whether or not the warning level $L_W$ is the second level. When it is determined in step f10 that the warning level $L_W$ is the second level, the processing proceeds to step f11, where a determination is made as to whether or not the warning generation flag $F_{WG}$ is set. When it is determined in step f11 that the warning generation flag $F_{WG}$ is not set, the warning generation flag $F_{WG}$ is set in step f12 and the warning change-over timer begins counting up, and a determination is made in step f13 as to whether or not the count value $T_{CW}$ of the warning change-over timer exceeds the first preset time $T_{WL}$.

When it is determined in step f13 that the count value $T_{CW}$ of the warning change-over timer is not more than the first preset time $T_{WL}$, the processing proceeds to step f9, where the visual warning means 28 is operated to display the warning mark 46 on the front window 27 to improve the awareness of the driver. When it is determined in step f11 that the warning generation flag $F_{WG}$ is set, the processing proceeds to step f13, where a determination is made again as to whether or not the count value $T_{CW}$ of the warning change-over timer exceeds the first preset time $T_{WL}$.

When it is determined in step f13 that the count value $T_{CW}$ of the warning change-over timer exceeds the first preset time $T_{WL}$, that is, the awareness of the driver is not improved by only the operation of the visual warning means 28, the processing proceeds to step f14, where the warning level $L_W$ is set to the third level, the warning generation flag $F_{WG}$ is reset in step f15 and the count value $T_{CW}$ of the warning change-over timer is reset to 0 in step f16, the auditory warning means 29 is operated in step f17 to sound the warning buzzer 48 to improve the awareness of the driver by auditory excitation, and then the processing returns to step f1 according to the next interrupt signal.

When it is determined in step f10 that the warning level $L_W$ is not the second level, the processing proceeds to step f18, where a determination is made as to whether or not the warning level $L_W$ is the third level. When it is determined in step f18 that the warning level $L_W$ is the third level, the processing proceeds to step f19, where a determination is made as to whether or not the warning generation flag $F_{WG}$ is set. When it is determined in step f19 that the warning generation flag $F_{WG}$ is set, the processing proceeds to step f17, where the auditory warning means 29 is operated to sound the warning buzzer 48 to improve the awareness of the driver. Further, when it is determined in step f19 that the warning generation flag $F_{WG}$ is not set, the processing proceeds to step f20, where the warning generation flag $F_{WG}$ is set, counting up of the warning change-over timer begins in step f21, and then the processing proceeds to step f17.

On the other hand, when it is determined in step f18 that the warning level $L_W$ is not the third level, the processing proceeds to step f22, where a determination is made as to whether or not the transition condition flag $F_{ST}$ is set. When it is determined that the transition condition flag $F_{ST}$ is set, operation of all three warning means 26, 28, and 29 is stopped in step f23, and the transition condition flag $F_{ST}$ is reset in step f24. When it is determined in step f22 that the transition condition flag $F_{ST}$ is not set, the processing returns to step f1 according to the next interrupt signal.

A steering wheel grip defect warning processing unit 35 incorporated in the warning control means 30 estimates a grip of the steering wheel 33 by the driver according to information of an input normal determination flag $F_{NI}$ which is set by the heartbeat processing means 13, 14, and 17 and controls the operation of the steering wheel grip defect warning means 34. When a condition where the input normal determination flag $F_{NI}$ is not set continues for a predetermined time, first, the steering wheel grip defect warning means 34 controls the tactile warning means 26 to alert the driver and, if unsuccessful, the steering wheel grip defect warning means 34 further operates the auditory warning means 29.

Figure 33:
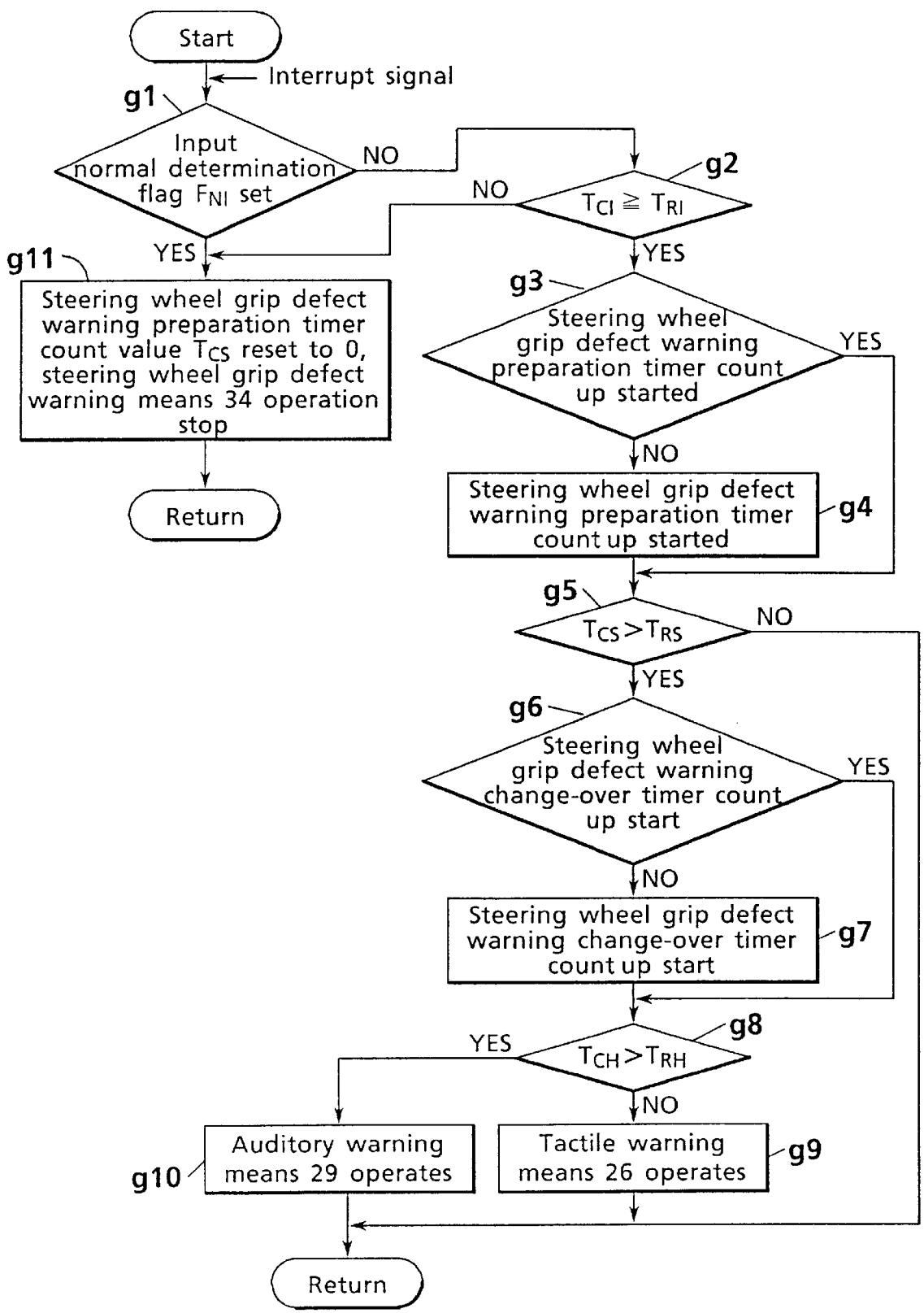
FIG. 33 is a flow chart showing processing performed by the steering wheel grip defect warning processing unit of the present embodiment.

Processing flow in the steering wheel grip defect processing unit 35 of the present embodiment according to information from the heartbeat processing means 17 is shown in FIG. 33. Specifically, processing by the steering wheel grip defect processing unit 35 in the present embodiment is carried out at every interrupt signal, for example, of 15 msec. First, a determination is made in step g1 as to whether or not the input normal determination flag $F_{NI}$ is set by the heartbeat processing means 13, 14, and 17, and when the input normal determination flag $F_{NI}$ is not set, that is, the driver's grip of the steering wheel 33 may be incorrect, the processing proceeds to step g2, where a determination is made as to whether or not the count value $T_{CI}$ of an input defect integrating timer is not less than a preset time $T_{RI}$.

When it is determined in step g2 that the count value $T_{CI}$ of the input defect integrating timer is not less than the preset time $T_{RI}$, a determination is made in step g3 as to whether or not counting up of a steering wheel grip defect warning preparation timer has begun. When it is determined that counting up of the steering wheel grip defect warning preparation timer has not begun, counting up of the steering wheel grip warning preparation timer has begun in step g4, and a determination is made in step g5 as to whether or not the count value $T_{CS}$ of the steering wheel grip defect warning preparation timer exceeds a preset time $T_{RS}$, for example, 2 seconds. Further, when it is determined in step g3 that counting up of the steering wheel grip defect warning preparation timer has begun, the processing proceeds to step g5, where a determination is made as to whether or not the count value $T_{CS}$ of the steering wheel grip defect warning preparation timer exceeds a preset time $T_{RS}$.

When it is determined in step g5 that the count value $T_{CS}$ of the steering wheel grip defect warning preparation timer exceeds a preset time $T_{RS}$, the processing proceeds to step g6, where a determination is made as to whether or not counting up of the steering wheel grip defect warning preparation timer has begun. When it is determined that counting up of the steering wheel grip defect warning preparation timer has not begun, the processing proceeds to step g7, where counting up of the steering wheel grip defect warning preparation timer is begun, and a determination is made in step g8 as to whether or not the count value $T_{CH}$ of the steering wheel grip defect warning change-over timer exceeds a preset time $T_{RH}$, for example, 3 seconds. Further, when it is determined in step g6 that the steering wheel defect warning change-over timer begins counting up, the processing proceeds to step g8, where a determination is made as to whether or not the count value $T_{CH}$ of the steering wheel grip defect warning change-over timer exceeds the preset time $T_{RH}$.

When it is determined in step g8 that the count value $T_{CH}$ of the steering wheel grip defect warning change-over timer is not more than the preset time $T_{RH}$, that is, a time duration where a grip of the steering wheel 33 is incorrect is short, the processing proceeds to step g9, where the tactile warning means 26 is operated to press or separate the side supports 44 to draw the driver's attention to grip the steering wheel 33 correctly, and the processing returns to step g1 according to the next interrupt signal.

When it is determined in step g8 that the count value $T_{CH}$ of the steering wheel grip defect warning change-over timer exceeds the preset time $T_{RH}$, that is, the driver's attention cannot be drawn by only the operation of the tactile warning means 26, the processing proceeds to step g10, where the auditory warning means 28 is operated, while pressing or separating the side supports 44 to the side of the driver, to sound the warning buzzer to draw the driver's attention to grip the steering wheel 33 correctly, by both tactile and auditory warning, and the processing returns to step g1 according to the next interrupt signal.

When it is determined in step g5 that the count value $T_{CS}$ of the steering wheel grip defect warning preparation timer is not more than the preset time $T_{RS}$, the processing returns to step g1 according to the next interrupt signal. When it is determined in step g1 that the input normal determination flag $F_{NI}$ is set, that is, the driver grips the steering wheel 33 correctly, or in step g2 that the count value $T_{CI}$ of the input defect integrating timer is less than the preset time $T_{RI}$, the processing proceeds to step g11, where the count value $T_{CS}$ of the steering wheel grip defect warning preparation timer is reset to 0, operation of the steering wheel grip defect warning means 34 is stopped, and the processing returns to step g1 according to the next interrupt signal.

The processing flow of the steering wheel grip defect warning processing unit 35 according to information from the heartbeat processing means 17 corresponding to the potential heartbeat sensor 16 has been described above with reference to FIG. 33. Similar warning processing may be performed in the steering wheel grip defect warning processing unit 35 according to information from the heartbeat processing means 13 and 14 corresponding to the infrared heartbeat sensors 11 and 12.

The reference value correction unit 32 determines according to a time from operation of the warning means 26, 28, and 29 to the driver's operation of the warning release switch 31, that the awareness of the driver is relatively high when the time is short, and corrects the reference heartbeat rate $R_{HB}$ and the reference warning change-over time $T_{BW}$ to higher values. On the other hand, when the time from operation of the warning means 26, 28, and 29 to the driver's operation of the warning is long, it determines that the awareness of the driver is lower than expected, corrects the reference heartbeat rate $R_{HB}$ and the reference warning change-over time $T_{BW}$ to lower values so that the warning means 26, 28, and 29 operate earlier, and outputs the corrected reference heartbeat rate $R_{HB}$ and the reference warning change-over time $T_{BW}$ individually to the heartbeat awareness determination means 19 and the steering awareness determination means 23.

Figure 34:
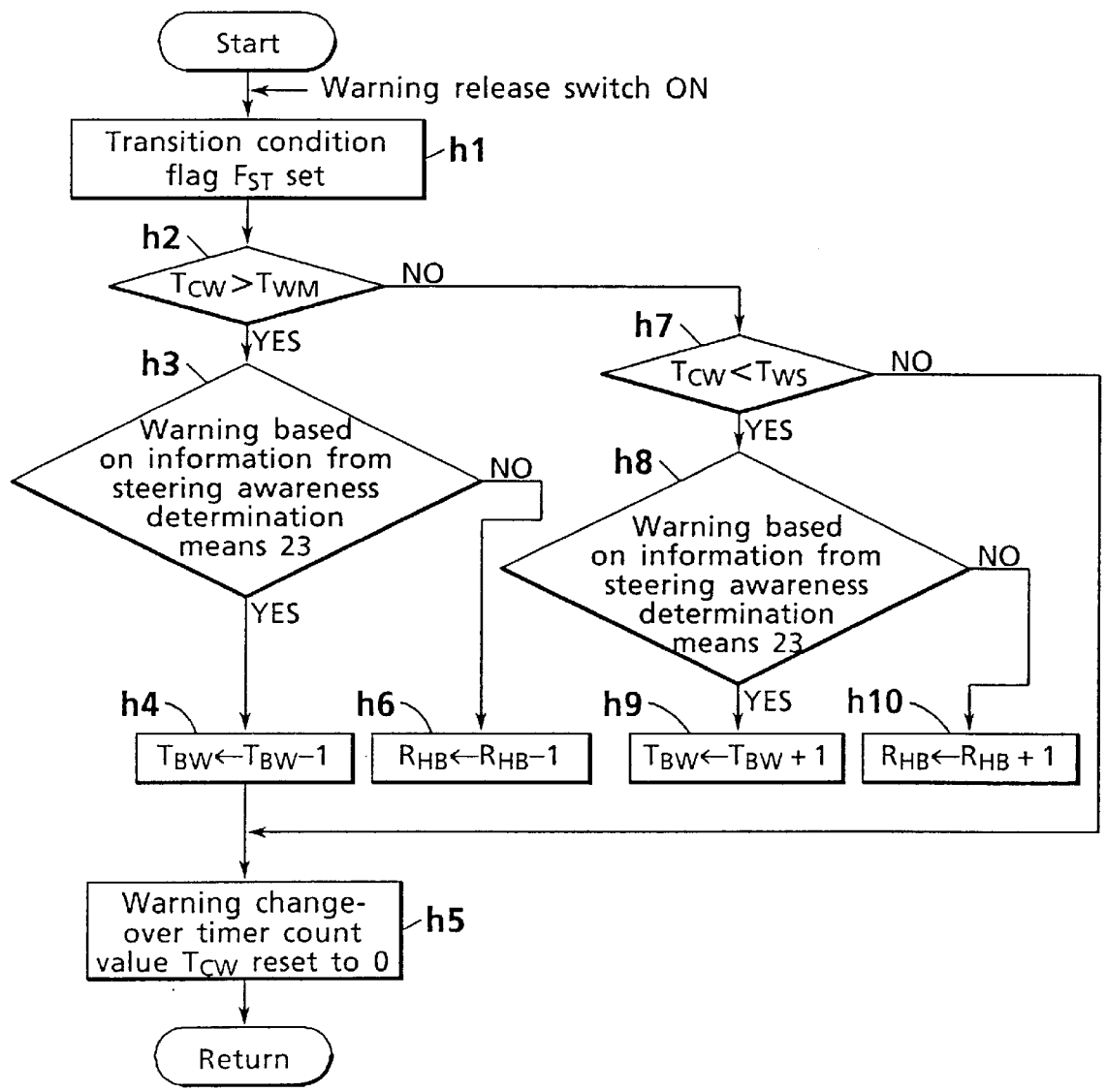
FIG. 34 is a flow chart showing processing performed by the reference value correction unit of the present embodiment.

Processing flow in the reference value correction unit 32 in the present embodiment is shown in FIG. 34. The processing in the reference value correction unit 32 in the present embodiment is begun by turning on the warning release switch 31. First, in step h1, the warning release flag $F_{ST}$ is set, and determination is made in step h2 as to whether or nor the count value $T_{CW}$ of the warning change-over timer exceeds a second preset time $T_{WM}$, for example, 6 seconds.

When it is determined in step h2 that the count value $T_{CW}$ of the warning change-over timer exceeds the second preset time $T_{WM}$, that is, reaction of the driver is not very fast, the processing proceeds to step h3, where a determination is made as to whether or not the present warning is a result of information from the steering awareness determination means 23. When it is determined that the warning is according to information from the steering awareness determination means 23, the processing proceeds to step h4, where the reference warning change-over time $T_{BW}$ is re-set to a 1 second smaller value so that the warning means 26, 28, and 29 operate earlier than before. Further, the count value $T_{CW}$ of the warning change-over timer is reset to 0, and then the processing returns to step h1 according to the next interrupt signal. When it is determined in step h3 that the present warning is not a result of information from the steering awareness determination means 23, that is, the warning is a result of information from the heartbeat awareness determination means 19, the processing proceeds to step h6, where the reference heartbeat rate $R_{HB}$ is re-set to a 1 smaller value so that the warning means 26, 28, and 29 operate sooner, and the count value $T_{CW}$ of the warning change-over timer is reset to 0.

On the other hand, when it is determined in step h2 that the count value $T_{CW}$ of the warning change-over timer is not more than the second preset time $T_{WM}$, the processing proceeds to step h7, where a determination is made as to whether or not the count value $T_{CW}$ of the warning change-over timer is shorter than a third preset time $T_{WS}$, for example, 2 seconds. When it is determined that the count value $T_{CW}$ of the warning change-over timer is shorter than the third preset time $T_{WS}$, that is, a reaction by the driver is very fast, the processing proceeds to step h8, where a determination is made as to whether or not the present warning is a result of information from the steering awareness determination means 23. When it is determined in step h8 that the present warning is a result of information from the steering awareness determination means 23, the processing proceeds to step h9, where the reference warning change-over time $T_{BW}$ is re-set to a 1 second greater value so that the warning means 26, 28, and 29 operate later, and then the processing proceeds to step h5. When it is determined in step h8 that the present warning is not a result of information from the steering awareness determination means 23, that is, the warning is according to information from the heartbeat awareness determination means 19, the processing proceeds to step h10, where the reference heartbeat rate $R_{HB}$ is re-set to 1 greater value so that the warning means 26, 28, and 29 operate later, and the processing proceeds to step h5.

When it is determined in step h7 that the count value $T_{CW}$ of the warning change-over timer is not less than the third preset time $T_{WS}$, the present reference heartbeat rate $R_{HB}$ and the reference warning change-over time $T_{BW}$ are unchanged, and the processing proceeds to step h5, where the count value $T_{CW}$ of the warning change-over timer is reset to 0.

The above embodiment may be used in any application for detecting the heartbeat rate of a person.

As described above, since the present invention includes an infrared type heartbeat sensor for detecting a heartbeat rate of the driver, a potential type heartbeat sensor for detecting the heartbeat rate of the driver from a potential difference due to pulsation between both hands, and heartbeat data processing means for comparing the heartbeat rate detected by the infrared type heartbeat sensor with heartbeat rate detected by the potential type heartbeat sensor, and selecting one as an effective heartbeat rate, even when the heartbeat rate cannot be detected by one of the heartbeat sensors, the heartbeat rate can be detected by the other heartbeat sensor, thereby preventing detection errors in the heartbeat rate and achieving positive and precise detection of the driver's heartbeat rate.

Further, since, in the heartbeat rate detection apparatus of the present invention, driver respiration variations are removed from the heartbeat rate calculated by the heartbeat processing means when determing the reference heartbeat rate, and as a result errors associated with driver respiration varations are eliminated, thereby obtaining reliable heartbeat data.

We claim:

1. An apparatus for detecting awareness of a vehicle driver, comprising:

an infrared type heartbeat sensor adapted to be disposed on a steering wheel of a vehicle for detecting heartbeat of a driver, a potential type heartbeat sensor adapted to be disposed on the steering wheel of the vehicle for detecting the heartbeat rate of the driver from a potential difference due to pulsation between both hands, heartbeat data processing means for comparing the heartbeat rate detected over a period of time by said infrared type heartbeat sensor with the heartbeat rate detected over the period of time by said potential type heartbeat sensor and adopting one as an effective heartbeat rate; and awareness determination means for determining a level of awareness of the vehicle driver according to the effective heartbeat rate adopted by the heartbeat data processing means.

2. The apparatus of claim 1, wherein, said potential type heartbeat sensor includes at least two electrodes.

3. The apparatus of claim 1, wherein, said heartbeat data processing means compares data of the heartbeat rate detected over a period of time by said infrared heartbeat sensor and the heartbeat rate detected over the period of time by said potential type heartbeat sensor, and adopts one of the two as the effective heartbeat rate.

4. The apparatus of claim 1, wherein,
a peripheral part of the infrared type heartbeat sensor is formed of an elastic member.

5. The apparatus of claim 1, wherein,
a contact surface of the infrared type heartbeat sensor with a hand of the driver is formed with a predetermined curvature according to a partial shape of the hand.

6. An apparatus for detecting awareness of a vehicle driver, comprising:
a heartbeat sensor for detecting heartbeat data;
heartbeat data processing means for calculating an average of said detected heartbeat data by averaging a number of said detected heartbeat data, said number corresponding to a number of heartbeats during one respiration of a person at rest to eliminate variations in heartbeat associated with respiration of said vehicle driver; and
awareness determination means for determining a level of awareness of said vehicle driver based on a variation of said calculated average of said detected heartbeat data within a predetermined period of time, the predetermined period of time being longer than a time period required to obtain said number of the detected heartbeat.

7. The apparatus of claim 6, wherein,
the heartbeat data processing means calculates the average heartbeat data by averaging at least two heartbeat data detected by said heartbeat sensor.

8. The apparatus of claim 7, wherein, said heartbeat data processing means sets the average heartbeat rate by calculating an average value of the past three to five heartbeat pulse intervals.

9. The apparatus of claim 8, wherein,
the heartbeat data processing means sets the average heartbeat rate by calculating an average value of past four heartbeat pulses.

10. The apparatus of claim 6, wherein,
the heartbeat sensor is adapted to be disposed on a steering wheel of the vehicle.

11. The apparatus of claim 6, wherein
said awareness determination means determines said level of awareness by calculating a reference heartbeat data when a variation of said detected heartbeat data is within a predetermined range and comparing said detected heartbeat data with said reference heartbeat data.

12. A method for detecting awareness of a vehicle driver comprising the steps of:
detecting heartbeat rates from intervals of heartbeat pulses by a heartbeat sensor;
calculating an average heartbeat rate by averaging a number of the detected heartbeat rates corresponding to a number of heartbeats in a single respiration to eliminate variations in heartbeat rates associated with respiration of the vehicle driver;
determining a level of awareness of the vehicle driver based on a variation in said average heartbeat rate within a predetermined period of time, the predetermined period of time being longer than a time period required to obtain said number of the detected heartbeat rates.

13. The method of claim 12, wherein,
the average heartbeat rate is calculated based on intervals of at least three to five heartbeat pulses.

14. An apparatus for detecting awareness of a vehicle driver, comprising:
heartbeat data processing means including,
a heartbeat sensor for detecting a heartbeat rate,
heartbeat rate setting means for setting an average heartbeat rate calculating an average value of heartbeats of past several times to eliminate variations in heartbeat rate associated with respiration of the vehicle driver,
peak point heartbeat rate calculating means for calculating a peak point heartbeat rate, where the average heartbeat rate changes from increasing to decreasing or from decreasing to increasing,
reference heartbeat rate calculating means for calculating a predetermined time average heartbeat rate as a reference heartbeat rate when a variation range of the average heartbeat rate falls within a predetermined range, and
awareness determination means for comparing the reference heartbeat rate with a current heartbeat rate when the peak point heartbeat rate is smaller than the reference heartbeat rate to determine a level of awareness of the driver.

15. The apparatus of claim 14, wherein,
the heartbeat sensor is an infrared type heartbeat sensor.

16. The apparatus of claim 14, wherein,
the heartbeat sensor is a potential type heartbeat sensor for detecting the heartbeat rate from a potential difference due to pulsation between both hands of the driver.

17. The apparatus of claim 14, wherein,
the heartbeat sensors are an infrared type sensor and a potential type sensor.

18. The apparatus of claim 17, wherein,
the heartbeat data processing means compares data of the heartbeat rate detected over a period of time by the infrared type heartbeat sensor with data of the heartbeat rate detected over the period of time by the potential type heartbeat sensor and adopts a greater value as an effective heartbeat rate.

19. The apparatus of claim 14, wherein,
the awareness determination means determines the driver to be in awareness condition when the average heartbeat rate varies more than the reference heartbeat rate within a predetermined period of time, and determines the driver to be in a sleep drive condition when the average heartbeat rate is smaller than the reference heartbeat rate continuously for more than the predetermined period of time.

20. The apparatus of claim 14, wherein,
the heartbeat sensor is adapted to be disposed on a steering wheel of the vehicle.

21. A method for detecting awareness of a vehicle driver, comprising:
(a) detecting over a period of time a plurality of signals indicative of pulses representing a heartbeat rate of the driver by using a plurality of sensors;

(b) integrating a predetermined number of pulse intervals of the plurality of signals detected over the period of time;

(c) comparing the integrated values with each other and selecting the smaller integrated value as an effective value; and (d) determining a level of awareness of the driver according to the selected integrated value.

22. The method of claim 21, further comprising the step of:

(e) giving a warning to the driver when the driver is not in an awareness condition according to the level of awareness of the driver.

23. The method of claim 21, wherein the step (b) comprises the substeps of:

determining every time a new pulse detection time as to whether or not an interval between the newly detected pulse and the previous pulse detection time is within a predetermined interval, and interpolating when the time interval is not within the predetermined interval.

24. The method of claim 23, wherein, the interpolating step suspends the integration when a currently detected interval is smaller than the predetermined interval, and cancels the currently detected interval when a sum of the currently detected interval and the next detected interval is equal to the previously detected interval, and suspends the integration when the currently detected interval is greater than the predetermined interval and adds half of a next detected interval to the integrated value.

25. The method of claim 21, wherein, said step (a) comprises the substep of:

detecting the plurality of signals by infrared type sensors.

26. The method of claim 21, wherein, said step (a) comprises the substep of:

detecting the plurality of signals by an infrared type sensor and a potential type heartbeat sensor for detecting the heartbeat rate from a potential generated due to pulsation between both hands of the driver.

* * * * *